United States Patent
Dropulic et al.

(10) Patent No.: US 10,639,329 B2
(45) Date of Patent: May 5, 2020

(54) METHOD TO TREAT CANCER WITH ENGINEERED T-CELLS

(71) Applicant: Lentigen Technology, Inc., Gaithersburg, MD (US)

(72) Inventors: Boro Dropulic, Ellicott City, MD (US); Rimas Orentas, Washington, DC (US); Dina Schneider, Potomac, MD (US); Winfried Krueger, Kensington, MD (US)

(73) Assignee: LENTIGEN TECHNOLOGY, INC., Gaithersburg, MD (US)

( * ) Notice: Subject to any disclaimer, the term of this patent is extended or adjusted under 35 U.S.C. 154(b) by 0 days.

(21) Appl. No.: 15/735,921

(22) PCT Filed: Jun. 12, 2016

(86) PCT No.: PCT/US2016/037120
§ 371 (c)(1),
(2) Date: Dec. 12, 2017

(87) PCT Pub. No.: WO2016/201394
PCT Pub. Date: Dec. 15, 2016

(65) Prior Publication Data
US 2019/0134091 A1    May 9, 2019

Related U.S. Application Data

(60) Provisional application No. 62/175,003, filed on Jun. 12, 2015.

(51) Int. Cl.
| | | |
|---|---|---|
| C07K 16/28 | (2006.01) | |
| A61K 39/395 | (2006.01) | |
| A61K 35/17 | (2015.01) | |
| C12N 5/0783 | (2010.01) | |
| C07K 14/725 | (2006.01) | |
| A61K 38/17 | (2006.01) | |
| A61K 35/15 | (2015.01) | |
| A61K 39/00 | (2006.01) | |

(52) U.S. Cl.
CPC .............. *A61K 35/17* (2013.01); *A61K 35/15* (2013.01); *A61K 38/177* (2013.01); *A61K 38/1774* (2013.01); *A61K 39/0011* (2013.01); *C07K 14/7051* (2013.01); *C12N 5/0636* (2013.01); *C07K 2319/03* (2013.01); *C12N 2502/1121* (2013.01); *C12N 2510/00* (2013.01); *C12N 2740/16043* (2013.01)

(58) Field of Classification Search
None
See application file for complete search history.

(56) References Cited

U.S. PATENT DOCUMENTS

| | | |
|---|---|---|
| 3,060,165 A | 10/1962 | Craig |
| 3,896,111 A | 7/1975 | Kupchan |
| 4,137,230 A | 1/1979 | Hashimoto |
| 4,151,042 A | 4/1979 | Higashide |
| 4,235,871 A | 11/1980 | Papahadjopoulos |
| 4,248,870 A | 2/1981 | Miyashita |
| 4,256,746 A | 3/1981 | Miyashita |
| 4,260,608 A | 4/1981 | Miyashita |
| 4,265,814 A | 5/1981 | Hashimoto |
| 4,294,757 A | 10/1981 | Asai |
| 4,307,016 A | 12/1981 | Asai |
| 4,308,268 A | 12/1981 | Miyashita |
| 4,308,269 A | 12/1981 | Miyashita |
| 4,309,428 A | 1/1982 | Miyashita |
| 4,313,946 A | 2/1982 | Powell |
| 4,315,929 A | 2/1982 | Freedmna |
| 4,317,821 A | 3/1982 | Miyashita |
| 4,322,348 A | 3/1982 | Asai |
| 4,331,598 A | 5/1982 | Hasegawa |
| 4,361,650 A | 11/1982 | Asai |
| 4,362,663 A | 12/1982 | Kida |
| 4,364,866 A | 12/1982 | Asai |
| 4,371,533 A | 2/1983 | Akimoto |
| 4,424,219 A | 1/1984 | Hashimoto |
| 4,450,254 A | 5/1984 | Isley |
| 4,486,414 A | 12/1984 | Pettit |
| 4,501,728 A | 2/1985 | Geho |
| 4,689,401 A | 8/1987 | Ferris |
| 4,816,444 A | 3/1989 | Pettit |

(Continued)

FOREIGN PATENT DOCUMENTS

| | | |
|---|---|---|
| EP | 0425235 | 5/1991 |
| JP | 2014514927 | 6/2014 |

(Continued)

OTHER PUBLICATIONS

Dotti et al., Immunological Reviews vol. 257, Issue 1, Version ofllecord online: Dec. 13, 2013 Design and development of therapies using chimeric antigen receptor-expressing T cells pp. 107-126.*
Abate-Daga et al., CAR models: next-generaton CAR modifications for enhanced I-cell funcion. Molecular Therapy—Oncolytics (2016) pp. 1-7).*
International Search Report and Written Opinion for PCT/US2016/037120 dated Oct. 31, 2016.
Leichtenstein et al., Lentiviral Vectors for Cancer Immunotherapy and Clinical Applications (Jul. 2, 2013) vol. 5, pp. 815-837.
Supplemental European Search Report issued in EP16808492 dated Nov. 8, 2018.

(Continued)

*Primary Examiner* — Maria G Leavitt
(74) *Attorney, Agent, or Firm* — Serge Sira, Esq.; Gregory J. Hwa, Esq.; Fish & Richardson P.C.

(57) ABSTRACT

Novel adoptive immunotherapy compositions comprising co-cultured lentiviral vector-transduced autologous antigen presentation cells and T cells are provided herein as well as are methods of use of same in a patient-specific combination immunotherapy that can be used to treat cancers and other diseases and conditions.

6 Claims, 2 Drawing Sheets

Specification includes a Sequence Listing.

(56) References Cited

U.S. PATENT DOCUMENTS

| | | |
|---|---|---|
| 4,837,028 A | 6/1989 | Allen |
| 4,879,278 A | 11/1989 | Pettit |
| 4,880,935 A | 11/1989 | Thorpe |
| 4,902,505 A | 2/1990 | Pardridge |
| 4,957,735 A | 9/1990 | Huang |
| 4,978,744 A | 12/1990 | Pettit |
| 4,986,988 A | 1/1991 | Pettit |
| 5,004,697 A | 4/1991 | Pardridge |
| 5,019,369 A | 5/1991 | Presant |
| 5,055,303 A | 10/1991 | Riley, Jr. |
| 5,076,973 A | 12/1991 | Pettit |
| 5,079,163 A | 1/1992 | Piatak, Jr. |
| 5,122,368 A | 5/1992 | Greenfield |
| 5,138,036 A | 8/1992 | Pettit |
| 5,188,837 A | 2/1993 | Domb |
| 5,208,020 A | 5/1993 | Chari |
| 5,208,021 A | 5/1993 | Johnson |
| 5,254,342 A | 10/1993 | Shen |
| 5,268,164 A | 12/1993 | Kozarich |
| 5,271,961 A | 12/1993 | Mathiowitz |
| 5,410,024 A | 4/1995 | Pettit |
| 5,413,797 A | 5/1995 | Khan |
| 5,416,064 A | 5/1995 | Chari |
| 5,449,752 A | 9/1995 | Fujii |
| 5,504,191 A | 4/1996 | Pettit |
| 5,506,206 A | 4/1996 | Kozarich |
| 5,514,670 A | 5/1996 | Friedman |
| 5,521,284 A | 5/1996 | Pettit |
| 5,530,097 A | 6/1996 | Pettit |
| 5,534,496 A | 7/1996 | Lee |
| 5,554,725 A | 9/1996 | Pettit |
| 5,599,902 A | 2/1997 | Pettit |
| 5,622,929 A | 4/1997 | Willner |
| 5,635,483 A | 6/1997 | Pettit |
| 5,663,149 A | 9/1997 | Pettit |
| 5,665,860 A | 9/1997 | Pettit |
| 5,780,588 A | 7/1998 | Pettit |
| 5,792,458 A | 8/1998 | Johnson |
| 5,824,805 A | 10/1998 | King |
| 6,034,065 A | 3/2000 | Pettit |
| 6,214,345 B1 | 4/2001 | Firestone |
| 6,239,104 B1 | 5/2001 | Pettit |
| 6,323,315 B1 | 11/2001 | Pettit |
| 6,441,163 B1 | 8/2002 | Chari |
| 6,884,869 B2 | 4/2005 | Senter |
| 7,338,929 B2 | 3/2008 | Debinski |
| 7,964,567 B2 | 6/2011 | Doronina |
| 1,042,181 A1 | 9/2019 | Orentas |
| 2002/0197266 A1 | 12/2002 | Debinski |
| 2003/0059854 A1* | 3/2003 | Means ............... A61K 49/0004 435/7.9 |
| 2005/0238649 A1 | 10/2005 | Doronina |
| 2006/0024317 A1 | 2/2006 | Boyd |
| 2006/0074008 A1 | 4/2006 | Senter |
| 2011/0070248 A1 | 3/2011 | Ichikawa |
| 2011/0212088 A1 | 9/2011 | Sabbadini |
| 2012/0213783 A1 | 8/2012 | Rosenberg |
| 2014/0112956 A1 | 4/2014 | Karlsson-Parra et al. |
| 2014/0134720 A1* | 5/2014 | Stauss ................ C07K 14/7051 435/328 |

FOREIGN PATENT DOCUMENTS

| | | |
|---|---|---|
| WO | WO 2004010957 | 2/2004 |
| WO | 2006/065495 | 6/2006 |
| WO | WO 2012079000 | 6/2012 |
| WO | WO13/126726 | 8/2013 |
| WO | WO14/082729 | 6/2014 |
| WO | 2014/186469 | 11/2014 |
| WO | WO15/063069 | 5/2015 |

OTHER PUBLICATIONS

Ahmad, et al., "scFv antibody: principles and clinical application," Clin. Dev. Immunol., 2012, 980250, 15 pages.

Al-Lazikani, et al., "Standard conformations for the canonical structures of immunoglobulins," J. Mol. Biol., 1997, 273:927-948.

Bierer, et al., "Cyclosporin A and FK506: molecular mechanisms of immunosuppression and probes for transplantation biology," Curr. Opin. Immun., 1993, 5:763-773.

Bird, et al., "Single-chain antigen-binding proteins," Science, 1988, 242:423-426.

Brentjens, et al., "Treatment of Chronic Lymphocytic Leukemia With Genetically Targeted Autologous T Cells: Case Report of an Unforeseen Adverse Event in a Phase I Clinical Trial," Mol. Ther., 2010, 18(4):666-668.

Brown, et al., "Stem-like tumor-initiating cells isolated from IL13Rα2 expressing gliomas are targeted and killed by IL13-zetakine-redirected T Cells," Clin Cancer Res., 2012, 18(8):2199-2209.

Capecchi, "High efficiency transformation by direct microinjection of DNA into cultured mammalian cells," Cell, 1980, 22:479-488.

Clay, et al., "Efficient Transfer of a Tumor Antigen-Reactive TCR to Human Peripheral Blood Lymphocytes Confers Anti-Tumor Reactivity," J. Immunol, 1999, 163:507-513.

DeKosky, et al., "In-depth determination and analysis of the human paired heavy- and light-chain antibody repertoire," Nature Medicine, 2015, 21:86-91.

Di Stasi, et al., "Inducible apoptosis as a safety switch for adoptive cell therapy," N. Engl. J. Med., 2011, 365(18):1673-83.

Dubowchik and Walker, "Receptor-mediated and enzyme-dependent targeting of cytotoxic anticancer drugs," Pharmacol. Ther., 1999, 83:67-123.

Felgner, et al., "Lipofection: a highly efficient, lipid-mediated DNA-transfection procedure," Proc. Natl. Acad. Sci. USA,1987, 84:7413-7417.

Foster, et al.,"Antitumor activity of EBV-specific T lymphocytes transduced with a dominant negative TGF-beta receptor," J. Immunother., 2008, 31(5):500-5.

Funatsu, et al., "The complete amino acid sequence of the A-chain of Abrin-a, a toxic protein from the seeds of Abrus precatorius," Agr. Biol. Chem., 1988, 52:1095-1097.

Gallin, "Ionic channels in leukocytes," J. Leukoc. Biol., 1986, 39:241-254.

GenBank: AAA35664.1, "T lymphocyte surface glycoprotein (CD8-beta) precursor [Homo sapiens]," dated Apr. 27, 1993, 1 page.

Gillespie, et al., "Phase I open study of the effects of ascending doses of the cytotoxic immunoconjugate CMB-401 (hCTMO1-calicheamicin) in patients with epithelial ovarian cancer," Ann. Oncol., 2000, 11:735-741.

Goyal and Batra, "Inclusion of a furin-sensitive spacer enhances the cytotoxicity of ribotoxin restrictocin containing recombinant single-chain immunotoxins," Biochem., 2000, 345 Pt 2:247-254.

Graham, et al., "A new technique for the assay of infectivity of human adenovirus 5 DNA," Virology, 1973, 52:456-467.

Grupp, et al., "Chimeric Antigen Receptor—Modified T Cells for Acute Lymphoid Leukemia," N. Engl., J. Med., 2013, 368:1509-1518.

Hamers-Casterman, et al., "Naturally occurring antibodies devoid of light chains," Nature, 1993, 363:446-448.

Han, et al., "Chimeric antigen receptor-engineered T cells for cancer immunotherapy: progress and challenges," J. Hematol. Oncol, 2013, 6:47, 7 pages.

Han, et al., "Linking T-cell receptor sequence to functional phenotype at the single-cell level," Nature Biotechnology, 2014, 32:684-692.

Haso, et al., "Anti-CD22-chimeric antigen receptors targeting B cell precursor acute lymphoblastic leukemia," Blood, 2013, 121(7):1165-74.

Hegde, et al., "Combinational targeting offsets antigen escape and enhances effector functions of adoptively transferred T cells in glioblastoma," Mol. Ther., 2013, 21(11):2087-2101.

Henderson, et al., "Comparison of the effects of FK-506, cyclosporin A and rapamycin on IL-2 production," Immunol., 1991, 73:316-321.

Holliger, et al., ""Diabodies": small bivalent and bispecific antibody fragments," Proc. Natl. Acad. Sci., 1993, 90:6444 6448.

(56) References Cited

OTHER PUBLICATIONS

Huse, et al., "Generation of a large combinatorial library of the immunoglobulin repertoire in phage lambda," Science, 1989, 246:1275-1281.
Huston, et al., "Protein engineering of antibody binding sites: recovery of specific activity in an anti-digoxin single-chain Fv analogue produced in *Escherichia coli*," Proc. Natl. Acad. Sci., 1988, 85:5879-5883.
Ijntema, et al., "Hydroxyapatite microcarriers for biocontrolled release of protein drugs," Int. J. Pharm., 1994, 112:215-224.
Johnston, et al., "Sustained Delivery of Interleukin-2 from a Poloxamer 407 Gel Matrix Following Intraperitoneal Injection in Mice," Pharm. Res., 1992, 9:425-434.
Jurgens, et al., "Transduction of primary lymphocytes with Epstein-Barr virus (EBV) latent membrane protein-specific T cell receptor induces lysis of virus-infected cells: a novel strategy for the treatment of Hodgkin's disease and nasopharyngeal carcinoma," J. Clinical Immunology, 2006, 26:22-32.
Klein, et al., "High-velocity microprojectiles for delivering nucleic acids into living cells," Nature, 1987, 327:70-73.
Kloss, et al., "Combinatorial antigen recognition with balanced signaling promotes selective tumor eradication by engineered T cells," Nat. Biotechnol., 2013, 31(1):71-5.
Kochenderfer, et al., "B-cell depletion and remissions of malignancy along with cytokine-associated toxicity in a clinical trial of anti-CD19 chimeric-antigen-receptor-transduced T cells," Blood, 2012, 119(12):2709-20.
Laird and Groman, "Isolation and characterization of tox mutants of corynebacteriophage beta," J. Virol., 1976, 19:220-227.
Langer, "Polymer-controlled drug delivery systems," Acc. Chem. Res., 1993, 26:537-542.
Lanitis, et al., "Chimeric antigen receptor T Cells with dissociated signaling domains exhibit focused antitumor activity with reduced potential for toxicity in vivo," Cancer Immunol. Res., 2013, 1(1):43-53.
Lau, et al., "Conjugation of doxorubicin to monoclonal anti-carcinoembryonic antigen antibody via novel thiol-directed cross-linking reagents," Bioorg-Med-Chem., 1995, 3(10):1299-1304.
Lau, et al., "Novel doxorubicin-monoclonal anti-carcinoembryonic antigen antibody immunoconjugate activity in vitro," Bioorg-Med-Chem., 1995, 3(10):1305-12.
Lee, et al., "Calicheamicins, a novel family of antitumor antibiotics," J. Antibiot., 1989, 42:1070-87.
Lefranc, et al., "IMGT unique numbering for immunoglobulin and T cell receptor variable domains and Ig superfamily V-like domains," Dev. Comp. Immunol., 2003, 27:55-77.
Lehner, et al., "Redirecting T Cells to Ewing's Sarcoma Family of Tumors by a Chimeric NKG2D Receptor Expressed by Lentiviral Transduction or mRNA Transfection," PLoS One. 2012, 7(2):e31210.
Liepins, et al., "Serotonin modulated Ca++ dependent K+ channels in alloimmune effector cell lytic function," Immunopharmacol. Immunotoxicol., 1989, 11:165-178.
Liu, et al., "Calcineurin is a common target of cyclophilin-cyclosporin A and FKBP-FK506 complexes," Cell, 1991, 66:807-815.
Lonberg, "Fully human antibodies from transgenic mouse and phage display platforms," Curr. Opin. Immunol., 2008, 20:450-459.
Lonberg, "Human antibodies from transgenic animals," Nat. Biotech., 2005, 23:1117-1125.
Long, et al., "Lessons learned from a highly-active CD22-specific chimeric antigen receptor," Oncoimmunology, 2013, 2(4):e23621.
Milone, et al., "Chimeric receptors containing CD137 signal transduction domains mediate enhanced survival of T cells and increased antileukemic efficacy in vivo," Mol. Ther., 2009, 17(8):1453-1464.
Morgan, et al., "Case Report of a Serious Adverse Event Following the Administration of T Cells Transduced With a Chimeric Antigen Receptor Recognizing ERBB2," Molecular Therapy, 2010, 18(4):843-851.

NCBI RefSeq: NP_000064.1, "T-cell surface glycoprotein CD3 gamma chain precursor [*Homo sapiens*]," dated Mar. 15, 2015, 3 pages.
NCBI RefSeq: NP_000130.1, "High affinity immunoglobulin epsilon receptor subunit beta isoform 1 [*Homo sapiens*]," dated Mar. 15, 2015, 3 pages.
NCBI RefSeq: NP_000607.1, "T-cell surface glycoprotein CD4 isoform 1 precursor [*Homo sapiens*]," dated Mar. 15, 2015, 3 pages.
NCBI RefSeq: NP_000617.1, "B-cell antigen receptor complex-associated protein beta chain isoform 1 precursor [*Homo sapiens*]," dated Mar. 15, 2015, 3 pages.
NCBI RefSeq: NP_000723.1, "T-cell surface glycoprotein CD3 delta chain isoform A precursor [*Homo sapiens*]," dated Mar. 15, 2015, 3 pages.
NCBI RefSeq: NP_000724.1, "T-cell surface glycoprotein CD3 epsilon chain precursor [*Homo sapiens*]," dated Mar. 15, 2015, 3 pages.
NCBI RefSeq: NP_001552.2, "Tumor necrosis factor receptor superfamily member 9 precursor [*Homo sapiens*]," dated Mar. 15, 2015, 3 pages.
NCBI RefSeq: NP_001758.2, "T-cell surface antigen CD2 precursor [*Homo sapiens*]," dated Mar. 15, 2015, 3 pages.
NCBI RefSeq: NP_001759.3, "T-cell surface glycoprotein CD8 alpha chain isoform 1 precursor [*Homo sapiens*]," dated Mar. 15, 2015, 3 pages.
NCBI RefSeq: NP_001762.2, "B-cell receptor CD22 isoform 1 precursor [*Homo sapiens*]," dated Mar. 15, 2015, 3 pages.
NCBI RefSeq: NP_001774.1, "B-cell antigen receptor complex-associated protein alpha chain isoform 1 precursor [*Homo sapiens*]," dated Mar. 15, 2015, 3 pages.
NCBI RefSeq: NP_001806.2, "Carcinoembryonic antigen-related cell adhesion molecule 3 isoform 1 precursor [*Homo sapiens*]," dated Mar. 15, 2015, 3 pages.
NCBI RefSeq: NP_003318.1, "Tumor necrosis factor receptor superfamily member 4 precursor [homo sapiens]," dated Mar. 15, 2015, 3 pages.
NCBI RefSeq: NP_004097.1, "High affinity immunoglobulin epsilon receptor subunit gamma precursor [*Homo sapiens*]," dated Mar. 15, 2015, 3 pages.
NCBI RefSeq: NP_006130.1, "T-cell-specific surface glycoprotein CD28 isoform 1 precursor [*Homo sapiens*]," dated Mar. 15, 2015, 3 pages.
NCBI RefSeq: NP_036224.1, "Inducible T-cell costimulator precursor [*Homo sapiens*]," dated Mar. 15, 2015, 3 pages.
NCBI RefSeq: NP_055022.2, "T-cell surface glycoprotein CD5 precursor [*Homo sapiens*]," dated Mar. 15, 2015, 3 pages.
NCBI RefSeq: NP_932170.1, "T-cell surface glycoprotein CD3 zeta chain isoform 1 precursor [*Homo sapiens*]," dated Mar. 15, 2015, 3 pages.
Neville, et al., "Enhancement of immunotoxin efficacy by acid-cleavable cross-linking agents utilizing diphtheria toxin and toxin mutants," J. Biol. Chem., 1989, 264:14653-14661.
Nicolson & Blaustein, "The interaction of Ricinus communis agglutinin with normal and tumor cell surfaces," J. Biochim. Biophys. Acta, 1972, 266:543-547.
Olsnes, "Ricin and ricinus agglutinin, toxic lectins from castor bean," Methods Enzymol., 1978, 50:330-335.
Olsnes, et al., "Mechanism of action of the toxic lectins abrin and ricin," Nature, 1974, 249:627-631.
Orentas, et al., "Retroviral transduction of a T cell receptor specific for an Epstein-Barr virus-encoded peptide," Clinical Immunology, 2001, 98:220-228.
Park, et al., Treating cancer with genetically engineered T cells, Trends Biotechnol., 2011, 29:550-557.
Phillips, et al., "Targeting HER2-Positive Breast Cancer with Trastuzumab-DM1, an Antibody—Cytotoxic Drug Conjugate," Cancer Res., 2008, 68:9280-9290.
Poljak, et al., "Production and structure of diabodies," Structure, 1994, 2:1121-1123.
Porter, et al., "Chimeric antigen receptor-modified T cells in chronic lymphoid leukemia," N. Engl. J. Med., 2011, 365(8):725-33.

(56) References Cited

OTHER PUBLICATIONS

Rathore, et al., "Overproduction of fungal ribotoxin α-sarcin in *Escherichia coli*: generation of an active immunotoxin," Gene, 1997, 190:31-35.

Sheriff, et al., "Redefining the minimal antigen-binding fragment," Nat. Struct. Biol., 1996, 3:733-736.

Stirpe, et al., "Ribosome—Inactivating Proteins from Plants: Present Status and Future Prospects," Bio/Technology, 1992, 10:405-412.

Sun, et al., "Unbiased analysis of TCRA/B chains at the single-cell level in human CD8+ T-Cell subsets," PLoS One, 2012, 7:e40386.

Suzuki, et al., "Engineering receptor-mediated cytotoxicity into human ribonucleases by steric blockade of inhibitor interaction," Nat. Biotech., 1999, 17:265-70.

Thorpe, et al., "New copuling agents for the synthesis of immunotoxins containing a hindered disulfide bond with improved stability in vivo," Cancer Res., 1987, 47:5924-5931.

Till, et al., "Adoptive immunotherapy for indolent non-Hodgkin lymphoma and mantle cell lymphoma using genetically modified autologous CD20-specific T cells," Blood, 2008, 112:2261-2271.

Tumaini, et al., "Simplified process for the production of anti—CD19-CAR—engineered T cells," Cytotherapy, 2013, 15(11):1406-1417.

Ward, et al., "Binding activities of a repertoire of single immunoglobulin variable domains secreted from *Escherichia coli*," Nature, 1989, 341:544-546.

Winter and Harris, "Humanized antibodies," Immunol. Today, 1993, 14:243-246.

Yu, et al., "The biosynthetic gene cluster of the maytansinoid antitumor agent ansamitocin from Actinosynnema pretiosum," PNAS, 2002, 99:7968-7973.

Yvon, et al., "Immunotherapy of metastatic melanoma using genetically engineered GD2-specific T cells," Clin. Cancer Res., 2009, 15(18):5852-60.

Zhao, et al., "A herceptin-based chimeric antigen receptor with modified signaling domains leads to enhanced survival of transduced T lymphocytes and antitumor activity," J. Immunol., 2009, 183(9):5563-74.

Zhao, et al., "Primary Human Lymphocytes Transduced with NY-ESO-1 Antigen-Specific TCR Genes Recognize and Kill Diverse Human Tumor Cell Lines," J. Immunol., 2005, 174:4415-4423.

* cited by examiner

METHOD TO TREAT CANCER WITH ENGINEERED T-CELLS

CROSS-REFERENCE TO RELATED APPLICATIONS

This application is a 371 U.S. National Phase Application of PCT/US2016/037120, filed on Jun. 12, 2016, which claims the benefit of priority under 35 U.S.C. Section 119(e) to U.S. Provisional Patent Application No. 62/175,003, filed on Jun. 12, 2015. The entire contents of each of the foregoing applications is incorporated herein by reference.

SEQUENCE LISTING

The instant application contains a Sequence Listing which has been submitted electronically in ASCII format and is hereby incorporated by reference in its entirety. Said ASCII copy, created on Dec. 11, 2017, is named Sequence_Listing.txt and is 32 kilobytes in size.

FIELD OF THE DISCLOSURE

This application relates to the field of cancer, particularly to a composition comprising autologous antigen presentation cells transduced with lentiviral vectors expressing patient-specific mutated cancer transcripts co-cultured with autologous T cells transduced with chimeric antigen receptors (CARs) and methods of use in patient-specific combination immunotherapy.

BACKGROUND OF THE INVENTION

Cancer is one of the deadliest threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult. One of the difficulties in modern cancer treatments is the amount of time that elapses between a biopsy and the diagnosis of cancer, and effective treatment of the patient. During this time, a patient's tumor may grow unimpeded, such that the disease has progressed further before treatment is applied. This negatively affects the prognosis and outcome of the cancer.

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4): e23621). The antigen-binding motif of a CAR is commonly fashioned after a single chain Fragment variable (scFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al Clin Cancer Res. 2012; 18(8):2199-209; Lehner M et al. PLoS One. 2012; 7 (2): e31210). There remains significant work with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the scFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ξ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia. Blood. 2013; 121 (7):1165-74; Kochenderfer J N et al. Blood. 2012; 119 (12):2709-20). This is borne out by the clinical success of CD19-specific CARs that are in a second generation CD28/CD3-ξ (Lee D W et al. American Society of Hematology Annual Meeting. New Orleans, La.; Dec. 7-10, 2013) and a CD137/CD3-ξ signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured.

Current challenges in the more widespread and effective adaptation of CAR therapy for cancer relate to a paucity of compelling targets. Creating binders to cell surface antigens is now readily achievable, but discovering a cell surface antigen that is specific for tumor while sparing normal tissues remains a formidable challenge. One potential way to imbue greater target cell specificity to CAR-expressing T cells is to use combinatorial CAR approaches. In one system, the CD3-ξ and CD28 signal units are split between two different CAR constructs expressed in the same cell; in another, two CARs are expressed in the same T cell, but one has a lower affinity and thus requires the alternate CAR to be engaged first for full activity of the second (Lanitis E et al. Cancer Immunol Res. 2013; 1(1):43-53; Kloss C C et al. Nat Biotechnol. 2013; 31(1):71-5). A second challenge for the generation of a single scFv-based CAR as an immunotherapeutic agent is tumor cell heterogeneity. At least one group has developed a CAR strategy for glioblastoma whereby the effector cell population targets multiple antigens (HER2, IL-13Ra, EphA2) at the same time in the hope of avoiding the outgrowth of target antigen-negative populations (Hegde M et al. Mol Ther. 2013; 21(11):2087-101).

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with AP1903 demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-β by the expression of a decoy receptor further demonstrates that degree to which effector T cells can be engineered for optimal antitumor activity (Foster A E et al. J Immunother. 2008; 31(5):500-5).

Thus, while it appears that CARs can trigger T-cell activation in a manner similar to an endogenous T-cell receptor, a major impediment to the clinical application of this CAR-based technology to date has been limited in vivo expansion of CAR+ T cells, rapid disappearance of the cells after infusion, disappointing clinical activity, and the undue length of time between diagnosis and timely treatment of cancer using such CAR+ T cells.

Accordingly, there is an urgent and long felt need in the art for discovering compositions and methods for treatment of cancer using a CAR-based therapy that can exhibit patient-specific intended therapeutic attributes without the aforementioned short comings.

The present invention addresses these needs by providing compositions comprising co-cultured lentiviral vector transduced autologous antigen presentation cells/T cells and methods of use of same in a patient-specific combination therapy that can be used to treat cancers and other diseases and/or conditions.

In particular, the present invention as disclosed and described herein provides a composition comprising autologous antigen presentation cells transduced with lentiviral vectors expressing patient-specific tumor-encoded mutated cancer antigens, which cells are co-cultured with autologous T cells transduced with lentiviral vector expressed chimeric antigen receptors (CARs), either with or without one or more lentiviral expressed tumor biopsy and peripheral blood-derived tumor antigen T-cell receptors transduced into the therapeutic T cell population, to generate active patient-specific anti-tumor T-cell populations that can be infused directly back into the patient to promote in vivo expansion, persistence of patient-specific anti-tumor T-cells resulting in tumor stabilization, reduction, and/or elimination, and/or remission and/or elimination of cancer in a patient-specific manner.

SUMMARY OF THE INVENTION

Novel adoptive immunotherapy compositions comprising co-cultured lentiviral vector-transduced autologous antigen presentation cells and T cells are provided herein as well as are methods of use of same in a patient-specific combination immunotherapy that can be used to treat cancers and other diseases and conditions.

Thus, in one aspect, lentiviral vectors expressing patient-specific mutated cancer antigens, lentiviral vectors expressing native T Cell Receptors (TCRs), lentiviral vectors expressing tumor-specific reactive T cell TCR transcripts, and lentiviral vectors expressing chimeric antigen receptors (CARs) are provided herein, as well as host cells (e.g., T cells) expressing the mutated cancer antigens, the native T Cell Receptors, the T cell TCR transcripts, and the receptors, and nucleic acid molecules encoding the mutated cancer antigens, the native T Cell Receptors, the T cell TCR transcripts, and the receptors. Methods of using the disclosed lentiviral vectors expressing patient-specific mutated cancer antigens, lentiviral vectors expressing native T Cell Receptors (TCRs), lentiviral vectors expressing tumor-specific reactive T cell TCR transcripts, and lentiviral vectors expressing chimeric antigen receptors (CARs), host cells, and nucleic acid molecules are also provided, for example, to treat a cancer in a subject.

In one aspect, an adoptive immunotherapy composition is provided comprising an autologous T-cell population transduced with one or more lentiviral vectors encoding single or multiple chimeric antigen receptors (CAR), wherein the T cells are co-cultured with autologous antigen presentation cells transduced with one or more lentiviral vectors expressing patient-derived tumor antigens thereby generating an active patient-specific autologous anti-tumor T-cell population capable of promoting in vivo expansion, persistence of patient-specific anti-tumor T-cells resulting in tumor stabilization, reduction, and/or elimination, and/or remission and/or elimination of cancer in a patient-specific manner.

In one embodiment, the autologous antigen presentation cells are derived from autologous dendritic cells or B cells or a mixture or peripheral blood derived lymphocytes.

In one embodiment, an adoptive immunotherapy composition is provided wherein the autologous patient-specific T cells containing native T Cell Receptors (TCRs) are transduced with lentiviral vector to express chimeric antigen receptors (CARs) either during or after the co-culture with autologous antigen presentation cells transduced with one or more lentiviral vectors expressing patient-derived tumor antigens to generate an active patient-specific autologous anti-tumor T-cell population capable of promoting in vivo expansion, persistence of patient-specific anti-tumor T-cells resulting in tumor stabilization, reduction, and/or elimination, and/or remission and/or elimination of cancer in a patient-specific manner.

In one embodiment, an adoptive immunotherapy composition is provided wherein the patient-derived tumor antigens are identified through patient biopsy and nucleotide sequencing to identify mutant RNA transcripts within the mutanome.

In one embodiment, an adoptive immunotherapy composition is provided wherein the autologous anti-tumor T-cell population(s) comprise autologous antigen presentation cells (APCs) comprising patient-specific dendritic cells or B cells, or a mixture or peripheral blood derived lymphocytes.

In another embodiment, an adoptive immunotherapy composition is provided wherein the autologous anti-tumor T-cell population(s) comprise autologous antigen presentation cells (APCs) comprising active patient-specific autologous B cells immortalized with Epstein-Barr Virus (EBV), wherein the immortalization step comprises culturing autologous B cells with an EBV-containing cell culture supernatant. In one embodiment, commercial services for production of such active patient-specific autologous B cells immortalized with EBV include, for example, and not by way of limitation, Applied Biologic Material, ABM, Inc., (abmgood.com/EBV-Cell-Immortalization.html). In one embodiment, the EBV immortalized B cell line comprises the cell line routinely used in the art including, and not by way of limitation, EBV immortalized B cell line B95-8

(ATCC CRL-1612, or alternatively the EBV-containing supernatant (ATCC-BR14-92).

In another aspect, an adoptive immunotherapy composition is provided comprising an autologous T-cell population transduced with a one or more lentiviral vectors encoding single or multiple chimeric antigen receptors, wherein the T-cell population is additionally transduced with one or more lentiviral vectors encoding tumor-specific T-cell receptors (TCRs) to generate an active patient-specific autologous anti-tumor T-cell population capable of promoting in vivo expansion, persistence of patient-specific anti-tumor T-cells resulting in tumor stabilization, reduction, and/or elimination, and/or remission and/or elimination of cancer in a patient-specific manner.

In one embodiment, an adoptive immunotherapy composition is provided wherein the tumor-specific T-cell receptors (TCRs) were first identified by co-culturing antigen presentation cells (APCs) transduced with one or more lentiviral vectors expressing patient-derived tumor antigens with the HLA-compatible or patient specific T cells.

In one embodiment, the autologous antigen presentation cells are derived from autologous dendritic cells or B cells or a mixture or peripheral blood derived lymphocytes.

In one embodiment, an adoptive immunotherapy composition is provided wherein the tumor-specific T-cell receptors (TCRs) are HLA-compatible or patient-specific.

In one embodiment, an adoptive immunotherapy composition is provided wherein the autologous patient-specific T cells containing patient-specific, tumor-specific T Cell Receptor (TCR) are transduced with lentiviral vector to express chimeric antigen receptors (CARs) either during or after the co-culture with autologous antigen presentation cells transduced with one or more lentiviral vectors expressing patient-derived tumor antigens to generate an active patient-specific autologous anti-tumor T-cell population capable of recognizing said tumor-specific T-cell receptors (TCRs) and capable of promoting in vivo expansion, persistence of patient-specific anti-tumor T-cells resulting in tumor stabilization, reduction, and/or elimination, and/or remission and/or elimination of cancer in a patient-specific manner.

In one embodiment, an adoptive immunotherapy composition is provided wherein the patient-derived tumor antigens are identified through patient biopsy and nucleotide sequencing to identify mutant RNA transcripts within the mutanome. In one embodiment, the nucleotide sequencing is performed using Next Gen sequencing.

In one embodiment, an adoptive immunotherapy composition is provided wherein the autologous anti-tumor T-cell population(s) comprise autologous antigen presentation cells (APCs) comprising patient-specific dendritic cells or B cells, or a mixture or peripheral blood derived lymphocytes.

In certain embodiments, an adoptive immunotherapy composition is provided wherein the active patient-specific autologous anti-tumor T-cell population is generated within one day, three days, five days, seven days, ten days, fourteen days, twenty-one days, or one month of tumor biopsy and wherein the active patient-specific autologous anti-tumor T-cell population that can be infused back into a patient suffering from cancer and is capable of promoting in vivo expansion, persistence of patient-specific anti-tumor T-cells resulting in tumor stabilization, reduction, and/or elimination, and/or remission and/or elimination of cancer in a patient-specific manner.

In certain embodiments of both the aforementioned aspects, an adoptive immunotherapy composition is provided wherein the CAR comprises at least one extracellular antigen binding domain, at least one linker domain, at least one transmembrane domain, and at least one intracellular signaling domain.

In certain embodiments of both the aforementioned aspects, an adoptive immunotherapy composition is provided wherein the at least one extracellular antigen binding domain of the CAR comprises at least one single chain variable fragment of an antibody that binds to the antigen.

In certain embodiments of both the aforementioned aspects, an adoptive immunotherapy composition is provided wherein the at least one extracellular antigen binding domain of the CAR comprises at least one heavy chain variable region of an antibody that binds to the antigen.

In certain embodiments of both the aforementioned aspects, an adoptive immunotherapy composition is provided wherein the at least one extracellular antigen binding domain of the CAR, the at least one intracellular signaling domain of the CAR, or both are connected to the transmembrane domain by a linker or spacer domain.

In certain embodiments of both the aforementioned aspects, an adoptive immunotherapy composition is provided wherein the extracellular antigen binding domain of the CAR is preceded by a leader peptide.

In certain embodiments of both the aforementioned aspects, an adoptive immunotherapy composition is provided wherein the extracellular antigen binding domain of the CAR targets an antigen comprising CD19, CD20, CD22, ROR1, TSLPR, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or any combination thereof.

In certain embodiments of both the aforementioned aspects, an adoptive immunotherapy composition is provided wherein the extracellular antigen binding domain of the CAR comprises an anti-CD19 scFV antigen binding domain, an anti-CD20 scFV antigen binding domain, an anti-CD22 scFV antigen binding domain, an anti-ROR1 scFV antigen binding domain, an anti-TSLPR scFV antigen binding domain, an anti-mesothelin scFV antigen binding domain, an anti-CD33 scFV antigen binding domain, an anti-CD38 scFV antigen binding domain, an anti-CD123 (IL3RA) scFV antigen binding domain, an anti-CD138 scFV antigen binding domain, an anti-BCMA (CD269) scFV antigen binding domain, an anti-GPC2 scFV antigen binding domain, an anti-GPC3 scFV antigen binding domain, an anti-FGFR4 scFV antigen binding domain, an anti-c-Met scFV antigen binding domain, an anti-PMSA scFV antigen binding domain, an anti-glycolipid F77 scFV antigen binding domain, an anti-EGFRvIII scFV antigen binding domain, an anti-GD-2 scFV antigen binding domain, an anti-NY-ESo-1 TCR scFV antigen binding domain, an anti-MAGE A3 TCR scFV antigen binding domain, or an amino acid sequence with 85%, 90%, 95%, 96%, 97%, 98% or 99% identity thereof, or any combination thereof.

In certain embodiments of both the aforementioned aspects, an adoptive immunotherapy composition is provided wherein the linker or spacer domain of the CAR is derived from the extracellular domain of CD8, and is linked to the transmembrane domain.

In certain embodiments of both the aforementioned aspects, an adoptive immunotherapy composition is provided wherein the CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, CD271, TNFRSF19, or any combination thereof.

In certain embodiments of both the aforementioned aspects, an adoptive immunotherapy composition is provided wherein the at least one intracellular signaling domain further comprises a CD3 zeta intracellular domain.

In certain embodiments of both the aforementioned aspects, an adoptive immunotherapy composition is provided wherein the at least one intracellular signaling domain is arranged on a C-terminal side relative to the CD3 zeta intracellular domain.

In certain embodiments of both the aforementioned aspects, an adoptive immunotherapy composition is provided wherein the at least one intracellular signaling domain comprises a costimulatory domain, a primary signaling domain, or any combination thereof.

In certain embodiments of both the aforementioned aspects, an adoptive immunotherapy composition is provided wherein the at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or any combination thereof.

In one aspect, isolated nucleic acid molecules encoding patient-specific mutated cancer antigens, isolated nucleic acid molecules encoding a native T Cell Receptors (TCRs), isolated nucleic acid molecule encoding a tumor-specific reactive T cell TCR transcripts, or isolated nucleic acid molecules encoding chimeric antigen receptors (CARs) are provided herein.

In one aspect of the CARs used in the active patient-specific autologous anti-tumor T-cell population(s), the CARs are modified to express or contain a detectable marker for use in diagnosis, monitoring, and/or predicting the treatment outcome such as progression free survival of cancer patients or for monitoring the progress of such treatment.

In one embodiment of the CARs used in the active patient-specific autologous anti-tumor T-cell population(s), the nucleic acid molecule encoding the disclosed CARs can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, a baboon endogenous virus (BaEV) or a combination thereof.

In certain embodiments of the CARs used in the active patient-specific autologous anti-tumor T-cell population(s), the lentiviral vectors are pseudotyped with different viral glycoproteins (GPs) including for example, and not by way of limitation, amphotropic murine leukemia virus [MLV-A], GP164, gibbon ape leukemia virus [GALV], RD114, feline endogenous virus retroviral-derived GPs, and vesicular stomatitis virus [VSV], measles virus, fowl plague virus [FPV], Ebola virus [EboV], lymphocytic choriomeningitis virus [LCMV]) non retroviral-derived GPs, as well as chimeric variants thereof including, for example, and not by way of limitation, chimeric GPs encoding the extracellular and transmembrane domains of GALV or RD114 GPs fused to the cytoplasmic tail (designated TR) of MLV-A GP.

In certain embodiments of the CARs used in the active patient-specific autologous anti-tumor T-cell population(s), the vector further comprises a promoter wherein the promoter is an inducible promoter, a tissue specific promoter, a constitutive promoter, a suicide promoter or any combination thereof.

In yet another embodiment of the CARs used in the active patient-specific autologous anti-tumor T-cell population(s), the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect of the CARs used in the active patient-specific autologous anti-tumor T-cell population(s), host cells including the nucleic acid molecule encoding the CAR are also provided. In some embodiments, the host cell is a T cell, such as a primary T cell obtained from a subject. In one embodiment, the host cell is a CD8+ T cell.

In yet another embodiment, a pharmaceutical composition is provided comprising an anti-tumor effective amount of a population of active patient-specific autologous anti-tumor T-cell population(s) of a human having a cancer, wherein the cancer is a refractory cancer non-responsive to one or more chemotherapeutic agents. The cancer includes hematopoietic cancer, myelodysplastic syndrome, pancreatic cancer, head and neck cancer, cutaneous tumors, minimal residual disease (MRD) in acute lymphoblastic leukemia (ALL), acute myeloid leukemia (AML), lung cancer, breast cancer, ovarian cancer, prostate cancer, colon cancer, melanoma or other hematological cancer and solid tumors, or any combination thereof.

In yet another embodiment, a pharmaceutical composition is provided comprising an anti-tumor effective amount of a population of active patient-specific autologous anti-tumor T-cell population(s) of a human having a cancer, wherein the cancer includes a hematological cancer such as leukemia (e.g., chronic lymphocytic leukemia (CLL), acute lymphocytic leukemia (ALL), acute myeloid leukemia (AML), or chronic myelogenous leukemia (CML), lymphoma (e.g., mantle cell lymphoma, non-Hodgkin's lymphoma or Hodgkin's lymphoma) or multiple myeloma, or any combination thereof.

In yet another embodiment, a pharmaceutical composition is provided comprising an anti-tumor effective amount of a population of active patient-specific autologous anti-tumor T-cell population(s) of a human having a cancer, wherein the cancer includes an adult carcinoma comprising coral and pharynx cancer (tongue, mouth, pharynx, head and neck), digestive system cancers (esophagus, stomach, small intestine, colon, rectum, anus, liver, intrahepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In another aspect, methods of making active patient-specific autologous anti-tumor CAR-containing T cells are provided. The methods include transducing a T cell with a vector or nucleic acid molecule encoding i) one or more patient-specific mutated cancer antigen; ii) one or more patient-specific and tumor-specific TCR; and iii) one or more chimeric antigen receptors (CARs), or any combination thereof, that specifically binds an antigen, thereby making active patient-specific autologous anti-tumor CAR-containing T cells.

In yet another aspect, a method of generating a population of RNA-engineered T-cells is provided that comprises introducing an in vitro transcribed RNA or synthetic RNA of a nucleic acid molecule encoding a i) one or more patient-specific mutated cancer antigens; ii) one or more patient-specific and tumor-specific TCR; and iii) one or more chimeric antigen receptor (CARs), or any combination thereof, into a cell of a subject, thereby generating an active patient-specific autologous anti-tumor T-cell population capable of promoting in vivo expansion, persistence of patient-specific anti-tumor T-cells resulting in tumor stabilization, reduction, and/or elimination, and/or remission and/or elimination of cancer in a patient-specific manner.

In another aspect, a pharmaceutical composition is provided comprising an autologous T-cell population transduced with one or more lentiviral vectors encoding single or multiple chimeric antigen receptors (CARs), wherein the T-cells are co-cultured with autologous antigen presentation cells transduced with one or more lentiviral vectors expressing patient-derived tumor antigens thereby generating an active patient-specific autologous anti-tumor T-cell population capable of promoting in vivo expansion, persistence of patient-specific anti-tumor T-cells resulting in tumor stabilization, reduction, and/or elimination, and/or remission and/or elimination of cancer in a patient-specific manner.

In another aspect, a pharmaceutical composition is provided comprising an autologous T cell population transduced with one or more lentiviral vectors encoding single or multiple chimeric antigen receptors (CARs), wherein the T-cell population is additionally transduced with one or more lentiviral vectors encoding tumor-specific T-cell receptors (TCRs) to generate an active patient-specific autologous anti-tumor T-cell population capable of recognizing said tumor-specific T-cell receptors (TCRs) and capable of promoting in vivo expansion, persistence of patient-specific anti-tumor T-cells resulting in tumor stabilization, reduction, and/or elimination, and/or remission and/or elimination of cancer in a patient-specific manner.

In one embodiment, a pharmaceutical composition is provided wherein the T cells are T cells of a human having a hematological cancer.

In another embodiment, a pharmaceutical composition is provided wherein the hematological cancer is leukemia or lymphoma.

In another embodiment, a pharmaceutical composition is provided wherein the leukemia is chronic lymphocytic leukemia (CLL), acute lymphocytic leukemia (ALL), or chronic myelogenous leukemia (CML).

In another embodiment, a pharmaceutical composition is provided wherein the lymphoma is mantle cell lymphoma, non-Hodgkin's lymphoma or Hodgkin's lymphoma.

In another embodiment, a pharmaceutical composition is provided wherein the hematological cancer is multiple myeloma. In another embodiment, a pharmaceutical composition is provided wherein the human cancer includes an adult carcinoma comprising oral and pharynx cancer (tongue, mouth, pharynx, head and neck), digestive system cancers (esophagus, stomach, small intestine, colon, rectum, anus, liver, intrahepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In another aspect, a method is provided for treating a mammal having a disease, disorder or condition associated with an elevated expression of a tumor antigen, the method comprising administering to the subject a pharmaceutical composition comprising an anti-tumor effective amount of an autologous T-cell population transduced with one or more lentiviral vectors encoding single or multiple chimeric antigen receptors (CARs), wherein the T-cells are co-cultured with autologous antigen presentation cells transduced with one or more lentiviral vectors expressing patient-derived tumor antigens thereby generating an active patient-specific autologous anti-tumor T-cell population capable of promoting in vivo expansion, persistence of patient-specific anti-tumor T-cells resulting in tumor stabilization, reduction, and/or elimination, and/or remission and/or elimination of cancer in a patient-specific manner.

In another aspect, a method is provided for treating a mammal having a disease, disorder or condition associated with an elevated expression of a tumor antigen, the method comprising administering to the subject a pharmaceutical composition comprising an anti-tumor effective amount of an autologous T-cell population transduced with one or more lentiviral vectors encoding single or multiple chimeric antigen receptors (CARs), wherein the T-cell population is additionally transduced with one or more lentiviral vectors encoding tumor-specific T-cell receptors (TCRs) to generate an active patient-specific autologous anti-tumor T-cell population capable of recognizing said tumor-specific T-cell receptors (TCRs) which can be infused directly back into the patient to promote in vivo expansion, persistence of patient-specific anti-tumor T-cells resulting in tumor stabilization, reduction, and/or elimination, and/or remission and/or elimination of cancer in a patient-specific manner.

In certain embodiments, a method is provided herein the T cell has been preselected by virtue of expressing specific activation or memory-associated surface markers.

In certain embodiments, a method is provided herein wherein the T cell and dendritic cells are derived from a hematopoietic stem cell donor, and wherein the procedure is carried out in the context of hematopoietic stem cell transplantation.

In yet another aspect, a method is provided for generating a persisting population of genetically engineered active patient-specific autologous anti-tumor T-cell population(s) in a human diagnosed with cancer. In one embodiment, the method comprises administering to a human patient in need thereof one or more active patient-specific autologous anti-tumor T-cell population(s) described herein, wherein the persisting population of active patient-specific autologous anti-tumor T-cell population(s), or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the compositions comprising an active patient-specific autologous anti-tumor T-cell population(s) disclosed herein.

In yet another aspect, a kit is provided for making a composition comprising an active patient-specific autologous anti-tumor T-cell population(s) as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the active patient-specific autologous anti-tumor T-cell population(s), lentiviral vectors expressing patient-specific mutated cancer antigens, lentiviral vectors expressing native T Cell Receptors (TCRs), lentiviral vectors expressing tumor-specific reactive T cell TCR transcripts, and lentiviral vectors expressing chimeric antigen receptors (CARs), as well as host cells (e.g., T cells) expressing the mutated cancer antigens, the native T Cell Receptors, the T cell TCR transcripts, and the receptors, and nucleic acid molecules encoding the mutated cancer antigens, the native T Cell Receptors, the T cell TCR transcripts, and the receptors, host cells, and methods as described supra are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Definitions

Figure 1:
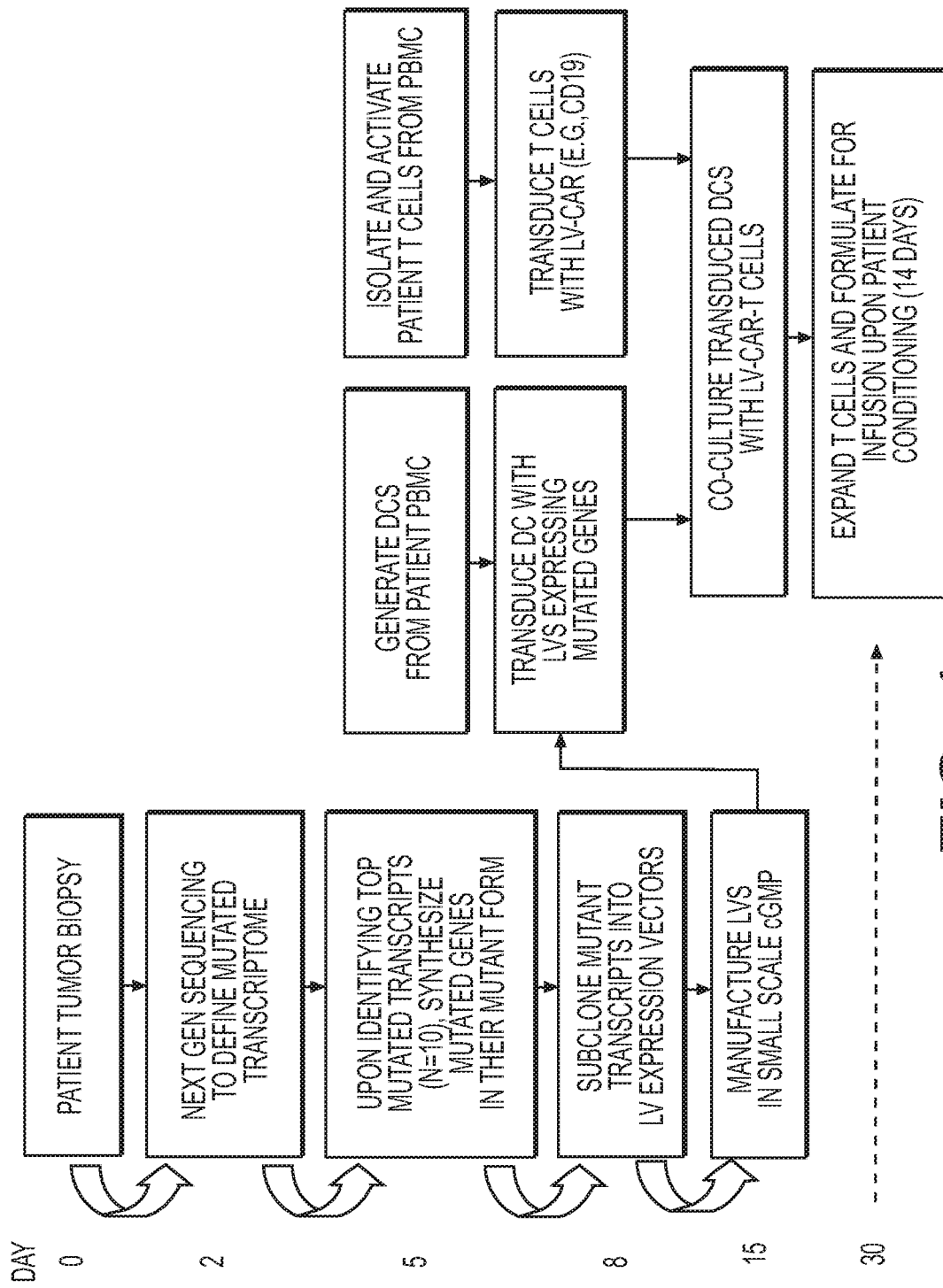
FIG. 1 depicts a first exemplary method to treat cancer, wherein T cells destined for immunotherapy (reinfusion into the patient) are transduced with a CAR-expression LV and stimulated by their native TCR to recognize patient-specific mutant proteins identified by next gen sequencing.
Figure 2:
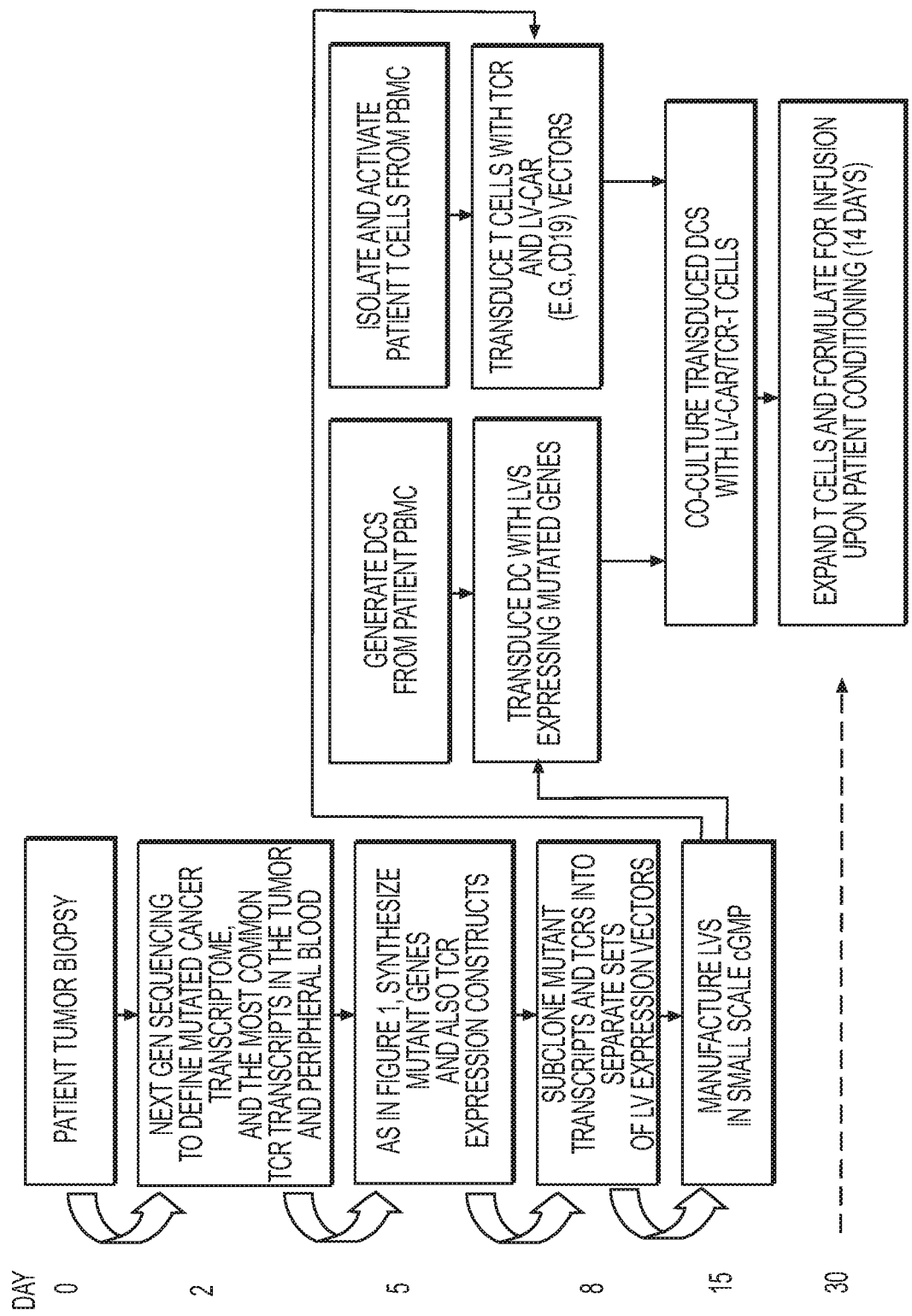
FIG. 2 depicts a second exemplary method to treat cancer, wherein T cells destined for immunotherapy (reinfusion into the patient) are transduced with a CAR-expression LV and TCR sequences derived from either tumor biopsy or blood, and stimulated by DCs expressing transcripts identified by Next Gen sequencing of the tumor.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of +/−20%, +/−10%, or more preferably +/−5%, or +/−1%, or still more preferably +/−0.1% from the specified value, as such variations are appropriate to perform the disclosed methods.

Unless otherwise noted, the technical terms herein are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: A Comprehensive Desk Reference*, published by VCH Publishers, Inc., 1995; and other similar references.

The present invention relates to compositions and methods for treating cancer including, but not limited to, hematologic malignancies and solid tumors. The present invention relates to a patient-specific, tumor-specific strategy of adoptive cell transfer of T cells transduced to express a chimeric antigen receptor (CAR).

The present invention relates more particularly to lentiviral vectors expressing patient-specific mutated cancer antigens, lentiviral vectors expressing native T Cell Receptors (TCRs), lentiviral vectors expressing tumor-specific reactive T cell TCR transcripts, and lentiviral vectors expressing chimeric antigen receptors (CARs) are provided herein, as well as host cells (e.g., T cells) expressing the mutated cancer antigens, the native T Cell Receptors, the T cell TCR transcripts, and the receptors, and nucleic acid molecules encoding the mutated cancer antigens, the native T Cell Receptors, the T cell TCR transcripts, and the receptors. Methods of using the disclosed lentiviral vectors expressing patient-specific mutated cancer antigens, lentiviral vectors expressing native T Cell Receptors (TCRs), lentiviral vectors expressing tumor-specific reactive T cell TCR transcripts, and lentiviral vectors expressing chimeric antigen receptors (CARs), host cells, and nucleic acid molecules are also provided, for example, to treat a cancer in a subject.

Surprisingly and unexpectedly, it has now been discovered by the inventors that the active anti-tumor population of T cells is more effective if, in addition to the expression of a tumor specific TCR (either by selection of native T cell populations or molecularly cloning and transfer of the tumor-specific TCR by means of a lentiviral vector), it is accompanied by the expression of a chimeric antigen receptor (CAR). The CAR surprisingly and unexpectedly allows for the persistence of the T cell population bearing the tumor-specific TCR(s) by virtue of stimulating this T cell population upon encountering a self-antigen (for example CD19) whose loss can be tolerated by the patient, and yet which serves to provide a stimulatory signal for the therapeutic cellular population that does not reside in the tumor tissue itself. Such active patient-specific anti-tumor T-cell populations as described herein can be infused directly back into the patient to promote in vivo expansion, persistence of patient-specific anti-tumor T-cells resulting in tumor stabilization, reduction, and/or elimination, and/or remission and/or elimination of cancer in a patient-specific manner.

Thus in its broadest aspect, the novelty of this adoptive immunotherapy lies in the use of Lentiviral vectors to identify patient TCRs by transducing APCs with tumor specific mutated genes and then culturing with patient T cells. This involves sequencing and identification of the mutated antigens in that patient and then expressing the mutated proteins in APCs via LVs and co-culturing T cells and identifying the patient TCRs. The mutatome specific TCRs and T cells can then be isolated and characterized. In addition, CARs are then added to enhance the immune response (IR). The differentiating feature is that the CAR is not the primary immunotherapy agent but acts to augment the TCR response that is highly specific. It augments the IR in two distinct ways: First, by providing the T cells with an additional signal to expand and survive in the body; and second, by targeting immunosuppressive cell antigens.

In another aspect, the novelty of this adoptive immunotherapy lies in the use of lentiviral vectors to identify patient-derived tumor-specific TCRs by transducing APCs with tumor encoded mutant genes using LV and then culturing with patient cells. This involves sequencing and identification of the mutated antigens from patients and then expressing the mutated protein in APCs by means of LV and co-culturing patient T cells to identify mutanome-specific TCRs. In another aspect, CARs are used to enhance the immune response to tumor mediated by the therapeutic T cell population. The immune response is enhanced in at least three ways. First, by providing the T cells an additional signal to expand and survive in the body, the CAR allows for the persistence of the therapeutic T cell population bearing the tumor-specific TCR(s) by virtue of stimulating the T cell population upon encountering self-antigen (for example CD19), whose loss can be tolerated by the patient, and yet which serves to provide a stimulatory signal for the therapeutic cellular population that does not reside in the tumor tissue itself. In a second aspect, the CAR may target cell-types other than the tumor that mediate immunosuppressive effects. For example, if CD19-expressing B cells are present in the tumor lesion and also mediate an anti-tumor effect the second benefit to the CAR-expressing tumor-specific T cell population is that the immunosuppressive cell population is also removed. In a third aspect the CAR targets an immunosuppressive population that is distal to the tumor, i.e. present in another compartment in the body. For example, using a CAR that targets myeloid derived suppressor cells (MDSCs), that may be present either in the tumor lesion itself or in the regional lymph nodes or bone marrow.

What follows is a detailed description of the CARs that may be used in the active patient-specific autologous anti-tumor T-cell population(s) disclosed herein, including a description of their extracellular domain, the transmembrane domain and the intracellular domain, along with additional description of CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one extracellular domain capable of binding to an antigen, at least one transmembrane domain, and at least one intracellular domain.

A chimeric antigen receptor (CAR) is an artificially constructed hybrid protein or polypeptide containing the antigen binding domains of an antibody (e.g., single chain variable fragment (scFv)) linked to T-cell signaling domains via a transmembrane domain. Characteristics of CARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR used in the active patient-specific autologous anti-tumor T-cell population(s) as disclosed herein, comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens are well known in the art and include, for example, a glioma-associated antigen, carcinoembryonic antigen (CEA), beta-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20, CD22, and CD37 are other candidates for target antigens in B-cell lymphoma. Some of these antigens (CEA, HER-2, CD19, CD20, CD22, idiotype) have been used as targets for passive immunotherapy with monoclonal antibodies with limited success.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen binding domain portion of the CAR targets an antigen that includes but is not limited to CD19, CD20, CD22, ROR1, Mesothelin, CD33, c-Met, PSMA, Glycolipid F77, EGFRvIII, GD-2, MY-ESO-1 TCR, MAGE A3 TCR, and the like.

Depending on the desired antigen to be targeted, the CAR can be engineered to include the appropriate antigen bind domain that is specific to the desired antigen target. For example, if CD19 is the desired antigen that is to be targeted, an antibody for CD19 can be used as the antigen bind domain incorporation into the CAR.

In one exemplary embodiment, the antigen binding domain portion of the CAR targets CD19. Preferably, the antigen binding domain in the CAR is anti-CD19 scFV, wherein the nucleic acid sequence of the anti-CD19 scFV comprises the sequence set forth in SEQ ID NO: 15 In one embodiment, the anti-CD19 scFV comprises the nucleic acid sequence that encodes the amino acid sequence of SEQ ID NO: 16. In another embodiment, the anti-CD19 scFV portion of the CAR comprises the amino acid sequence set forth in SEQ ID NO: 16.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus, Escherichia coli, Pseudomonas,* or *Salmonella*. Particularly, there is provided a CAR capable of binding to an antigen derived from an infectious bacterium, for example, *Helicobacter pyloris, Legionella pneumophilia,* a bacterial strain of *Mycobacteria* sps. (e.g. *M. tuberculosis, M. avium, M. intracellulare, M. kansaii,* or *M. gordonea*), *Staphylococcus aureus, Neisseria gonorrhoeae, Neisseria meningitides, Listeria monocytogenes, Streptococcus pyogenes,* Group A *Streptococcus,* Group B *Streptococcus (Streptococcus agalactiae), Streptococcus pneumoniae,* or *Clostridium tetani,* or a combination thereof.

2. Transmembrane Domain

In the CARs used in the active patient-specific autologous anti-tumor T-cell population(s) as disclosed herein, the CAR comprises one or more transmembrane domains fused to the extracellular domain of the CAR.

In one embodiment, an isolated nucleic acid molecule is provided wherein the encoded linker domain is derived from the extracellular domain of CD8, and is linked to the transmembrane domain.

In one embodiment, an isolated nucleic acid molecule is provided wherein the encoded linker domain is derived from the extracellular domain of the transmembrane domain and is linked to the transmembrane domain.

In some instances, the transmembrane domain can be selected or by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, CD271, TNFRSF19. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain in the CAR of the invention is the CD8 transmembrane domain. In one embodiment, the CD8 transmembrane domain comprises the nucleic acid sequence of SEQ ID NO: 3. In one embodiment, the CD8 transmembrane domain comprises the nucleic acid sequence that encodes the amino acid sequence of SEQ ID NO: 4. In another embodiment, the CD8 transmembrane domain comprises the amino acid sequence of SEQ ID NO: 4.

In some instances, the transmembrane domain of the CAR comprises the CD8.alpha.hinge domain. In one embodiment, the CD8 hinge domain comprises the nucleic acid sequence of SEQ ID NO: 5. In one embodiment, the CD8 hinge domain comprises the nucleic acid sequence that encodes the amino acid sequence of SEQ ID NO: 6. In another embodiment, the CD8 hinge domain comprises the amino acid sequence of SEQ ID NO: 6.

Without being intended to limit to any particular mechanism of action, it is believed that possible reasons for the enhanced therapeutic function associated with the exemplary CARs used in the active patient-specific autologous anti-tumor T-cell population(s) as disclosed herein of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

In one embodiment of the active patient-specific autologous anti-tumor T-cell population(s) as disclosed herein, non-limiting exemplary transmembrane domains for use in the CARs disclosed herein include the TNFRSF16 and TNFRSF19 transmembrane domains may be used to derive the TNFRSF transmembrane domains and/or linker or spacer domains as disclosed in Applicant's Provisional Patent Application No. 62/239,509, entitled CHIMERIC ANTIGEN RECEPTORS AND METHODS OF USE, as filed on Oct. 9, 2015, and assigned Miltenyi Biotech Technology, Inc. matter number LEN_015PRO, including, in particular, those other TNFRSF members listed within the tumor necrosis factor receptor superfamily as listed in Table I therein.

3. Spacer Domain

In the CARs used in the active patient-specific autologous anti-tumor T-cell population(s) as disclosed herein, a spacer domain can be arranged between the extracellular domain and the TNFRSF transmembrane domain, or between the intracellular domain and the TNFRSF transmembrane domain. The spacer domain means any oligopeptide or polypeptide that serves to link the TNFRSF transmembrane domain with the extracellular domain and/or the TNFRSF transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 118 to 178 (SEQ ID NO: 7) which is a hinge region of CD8.alpha. (NCBI RefSeq: NP.sub.--001759.3), amino acid numbers 135 to 195 of CD8.beta. (GenBank: AAA35664.1), amino acid numbers 315 to 396 of CD4 (NCBI RefSeq: NP.sub.--000607.1), or amino acid numbers 137 to 152 of CD28 (NCBI RefSeq: NP.sub.--006130.1) can be used. Also, as the spacer domain, a part of a constant region of an antibody H chain or L chain (CH1 region or CL region, for example, a peptide having an amino acid sequence shown in SEQ ID NO.: 8) can be used. Further, the spacer domain may be an artificially synthesized sequence.

Further, in the CAR, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 2).

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARS disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.--932170.1), amino acid numbers 45 to 86 of Fc.epsilon.RI.gamma. (NCBI RefSeq: NP.sub.--004097.1), amino acid numbers 201 to 244 of Fc.epsilon-.RI.beta. (NCBI RefSeq: NP.sub.--000130.1), amino acid numbers 139 to 182 of CD3.gamma. (NCBI RefSeq: NP.sub.--000064.1), amino acid numbers 128 to 171 of CD3.delta. (NCBI RefSeq: NP.sub.--000723.1), amino acid numbers 153 to 207 of CD3.epsilon. (NCBI RefSeq: NP.sub.--000724.1), amino acid numbers 402 to 495 of CD5 (NCBI RefSeq: NP.sub.--055022.2), amino acid numbers 707 to 847 of 0022 (NCBI RefSeq: NP.sub.--001762.2), amino acid numbers 166 to 226 of CD79a (NCBI RefSeq: NP.sub.--001774.1), amino acid numbers 182 to 229 of CD79b (NCBI RefSeq: NP.sub.--000617.1), and amino acid numbers 177 to 252 of CD66d (NCBI RefSeq: NP.sub.--001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.--001758.2), amino acid numbers 421 to 458 of CD4 (NCBI RefSeq: NP.sub.--000607.1), amino acid numbers 402 to 495 of CD5 (NCBI RefSeq: NP.sub.--055022.2), amino acid numbers 207 to 235 of CD8.alpha. (NCBI RefSeq: NP.sub.--001759.3), amino acid numbers 196 to 210 of CD83 (GenBank: AAA35664.1), amino acid numbers 181 to 220 of CD28 (NCBI RefSeq: NP.sub.--006130.1), amino acid numbers 214 to 255 of CD137 (4-1BB, NCBI RefSeq: NP.sub.--001552.2), amino acid numbers 241 to 277 of CD134 (OX40, NCBI RefSeq: NP.sub.--003318.1), and amino acid numbers 166 to 199 of ICOS (NCBI RefSeq: NP.sub.--036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 9 and the signaling domain of CD3-zeta comprises the nucleic acid sequence set forth in SEQ ID NO: 11.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 10 and the signaling domain of CD3-zeta comprises the nucleic acid sequence that encodes the amino acid sequence of SEQ ID NO: 12.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 10 and the signaling domain of CD3-zeta comprises the amino acid sequence set forth in SEQ ID NO: 12.

5. Additional Description of CARs

Also expressly included within the scope of the invention are functional portions of the CARs used in the active patient-specific autologous anti-tumor T-cell population(s) as disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively, or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, a-aminocyclohexane carboxylic acid, a-aminocycloheptane carboxylic acid, a-(2-amino-2-norbornane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Methods of generating chimeric antigen receptors, T cells including such receptors, and their use (e.g., for treatment of cancer) are known in the art and further described herein (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., Trends Biotechnol., 29:550-557, 2011; Grupp et al., N Engl J Med., 368:1509-1518, 2013; Han et al., J. Hematol Oncol., 6:47, 2013; Tumaini et al., Cytotherapy, 15, 1406-1417, 2013; Haso et al., (2013) Blood, 121, 1165-1174; PCT Pubs. WO2012/079000, WO2013/126726; and U.S. Pub. 2012/0213783, each of which is incorporated by reference herein in its entirety). For example, a nucleic acid molecule encoding a disclosed chimeric antigen binding receptor can be included in an expression vector (such as a lentiviral vector) used to transduce a host cell, such as a T cell, to make the disclosed CAR. In some embodiments, methods of using the chimeric antigen receptor include isolating T cells from a subject, transducing the T cells with an expression vector (such as a lentiviral vector) encoding the chimeric antigen receptor, and administering the CAR-expressing T cells to the subject for treatment, for example for treatment of a tumor in the subject.

B. Antibodies and Antigen Binding Fragments

One embodiment further provides a CAR used in the active patient-specific autologous anti-tumor T-cell population(s) disclosed herein, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6.sup.th ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, scFv, dsFv or Fab. References to "VL" or "VL" refer to the variable domain of an antibody light chain, including that of an Fv, scFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. scFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (scFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a scFv, is typically not decisive for scFvs. Thus, scFvs with both possible arrangements (VH-domain-linker domain-VL-domain; VL-domain-linker domain-VH-domain) may be used.

In a dsFv the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (MA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

The CARs used in the active patient-specific autologous anti-tumor T-cell population(s) disclosed herein, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}$I, $^{32}$P, $^{14}$C, $^3$H and $^{35}$S and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

The CAR used in the active patient-specific autologous anti-tumor T-cell population(s), a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MM), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MM). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}$H, $^{14}$C, $^{15}$N, $^{35}$S, $^{90}$Y, $^{99}$Tc, $^{111}$In, $^{125}$I, $^{131}$I.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In one embodiment, an isolated nucleic acid molecule encoding a chimeric antigen receptor (CARs) is provided comprising, from N-terminus to C-terminus, at least one extracellular antigen binding domain, at least one transmembrane domain, and at least one intracellular signaling domain.

In one embodiment of the CAR used in the active patient-specific autologous anti-tumor T-cell population(s), an isolated nucleic acid molecule encoding the CAR is provided wherein the encoded extracellular antigen binding domain comprises at least one single chain variable fragment of an antibody that binds to the antigen.

In another embodiment of the CAR used in the active patient-specific autologous anti-tumor T-cell population(s), an isolated nucleic acid molecule encoding the CAR is provided wherein the encoded extracellular antigen binding domain comprises at least one heavy chain variable region of an antibody that binds to the antigen.

In yet another embodiment of the CAR used in the active patient-specific autologous anti-tumor T-cell population(s), an isolated nucleic acid molecule encoding the CAR is provided wherein the encoded CAR extracellular antigen binding domain comprises at least one lipocalin-based antigen binding antigen (anticalins) that binds to the antigen.

In one embodiment of the CAR used in the active patient-specific autologous anti-tumor T-cell population(s), an isolated nucleic acid molecule is provided wherein the encoded extracellular antigen binding domain is connected to the transmembrane domain by a linker domain.

In another embodiment of the CARs used in the active patient-specific autologous anti-tumor T-cell population(s), an isolated nucleic acid molecule encoding the CAR is provided wherein the encoded extracellular antigen binding domain is preceded by a sequence encoding a leader or signal peptide.

In yet another embodiment of the CARs used in the active patient-specific autologous anti-tumor T-cell population(s), an isolated nucleic acid molecule encoding the CAR is provided wherein the encoded extracellular antigen binding domain targets an antigen that includes, but is not limited to, CD19, CD20, CD22, ROR1, mesothelin, CD33/IL3Ra, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or any combination thereof.

In certain embodiments of the CARs used in the active patient-specific autologous anti-tumor T-cell population(s), an isolated nucleic acid molecule encoding the CAR is provided wherein the encoded extracellular antigen binding domain comprises an anti-CD19 scFV antigen binding domain, an anti-CD20 scFV antigen binding domain, an anti-CD22 scFV antigen binding domain, an anti-ROR1 scFV antigen binding domain, an anti-TSLPR scFV antigen binding domain, an anti-mesothelin scFV antigen binding domain, an anti-CD33/IL3Ra scFV antigen binding domain, an anti-CD38 scFV antigen binding domain, an anti-CD123 (IL3RA) scFV antigen binding domain, an anti-CD138 scFV antigen binding domain, an anti-BCMA (CD269) scFV antigen binding domain, an anti-GPC2 scFV antigen binding domain, an anti-GPC3 scFV antigen binding domain, an anti-FGFR4 scFV antigen binding domain, an anti-c-Met scFV antigen binding domain, an anti-PMSA scFV antigen binding domain, an anti-glycolipid F77 scFV antigen binding domain, an anti-EGFRvIII scFV antigen binding domain, an anti-GD-2 scFV antigen binding domain, an anti-NY-ESo-1 TCR scFV antigen binding domain, an anti-MAGE A3 TCR scFV antigen binding domain, or an amino acid sequence with 85%, 90%, 95%, 96%, 97%, 98% or 99% identity thereof, or any combination thereof.

In one aspect of the CARs used in the active patient-specific autologous anti-tumor T-cell population(s), the CARs provided herein further comprise a linker domain.

In one embodiment of the CARs used in the active patient-specific autologous anti-tumor T-cell population(s), an isolated nucleic acid molecule encoding the CAR is provided wherein the extracellular antigen binding domain, the intracellular signaling domain, or both are connected to the transmembrane domain by a linker domain.

In one embodiment of the CARs used in the active patient-specific autologous anti-tumor T-cell population(s), an isolated nucleic acid molecule encoding the CAR is provided wherein the encoded linker domain is derived from the extracellular domain of CD8, and is linked to the transmembrane domain.

In yet another embodiment of the CARs used in the active patient-specific autologous anti-tumor T-cell population(s), an isolated nucleic acid molecule encoding the CAR is provided wherein the nucleic acid sequence encoding the transmembrane domain comprises a nucleotide sequence with 85%, 90%, 95%, 96%, 97%, 98% or 99% identity thereof.

In one embodiment of the CARs used in the active patient-specific autologous anti-tumor T-cell population(s), an isolated nucleic acid molecule encoding the CAR is provided wherein the encoded transmembrane domain comprises an amino acid sequence comprising at least one but not more than 10 modifications, or a sequence with 85%, 90%, 95%, 96%, 97%, 98% or 99% identity thereof.

In another embodiment of the CARs used in the active patient-specific autologous anti-tumor T-cell population(s), an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In yet another embodiment of the CARs used in the active patient-specific autologous anti-tumor T-cell population(s), an isolated nucleic acid molecule encoding the CAR is provided wherein the encoded intracellular signaling domain further comprises a CD3 zeta intracellular domain.

In one embodiment of the CAR disclosed herein, an isolated nucleic acid molecule encoding the CAR is provided wherein the encoded intracellular signaling domain is arranged on a C-terminal side relative to the CD3 zeta intracellular domain.

In another embodiment of the CARs used in the active patient-specific autologous anti-tumor T-cell population(s), an isolated nucleic acid molecule encoding the CAR is provided wherein the encoded at least one intracellular signaling domain comprises a costimulatory domain, a primary signaling domain, or a combination thereof.

In further embodiments of the CARs used in the active patient-specific autologous anti-tumor T-cell population(s), an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment of the CARs used in the active patient-specific autologous anti-tumor T-cell population(s), an isolated nucleic acid molecule encoding the CAR is provided that further contains a leader sequence or signal peptide sequence.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, Iowa, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.).

Bacteriophage vectors, such as λgT10, λgT11, λZapII (Stratagene), EMBL4, and λNMI 149, also can be used. Examples of plant expression vectors include pBI01, pBI101.2, pBHO1.3, pBI121 and pBIN19 (Clontech). Examples of animal expression vectors include pEUK-C1, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4+/CD8+ double positive T cells, CD4+ helper T cells, e.g., Thi and Th2 cells, CD8+ T cells (e.g., cytotoxic T cells), tumor infiltrating cells, memory T cells, na'ive T cells, and the like. The T cell may be a CD8+ T cell or a CD4+ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the CARs used in the active patient-specific autologous anti-tumor T-cell population(s) can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia (CLL), hairy cell leukemia, acute lymphocytic leukemia (ALL), acute myeloid leukemia (AML), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al, J. Immunol. 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example, topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a non-toxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy, adoptive immunotherapy, and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as Remington's Pharmaceutical Science, 19th ed., Mack Publishing Company, Easton, Pa. (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235, 871; 4,501,728; 4,837,028; 4,957,735; 5,019,369; 5,055, 303; 5,514,670; 5,413,797; 5,268,164; 5,004,697; 4,902, 505; 5,506,206; 5,271,961; 5,254,342 and 5,534,496).

G. Kits

In one aspect, Kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Next Gen Sequencing of the Tumor Mutanome

This procedure refers to Next Gen sequencing of patient tumor material, and identifying the mutated proteins present in the tumor (as a group, referred to as the mutanome). These sequences will be used as the basis for creating vectors that express mutant tumor proteins. When available, non-tumor-associated patient material will be used for normal comparison (such as peripheral blood), as will publically available databases of the human genome). The methods of Next Generation sequencing are a well-established technique in molecular biology and may be found, for example, in Vogelstein B, Papadopoulos N, Velculescu V E, et al., 2013, Cancer Genome Landscapes, Science 339:1546-1558.

The National Institutes of Health (NIH) has provided on-line the Cancer Genome Atlas (cancergenome.nih.gov). Therein can be found comprehensive maps of the key genomic changes in 33 types of cancer. The data is pipelined to the NIH through specific TCGA (The Cancer Genome Atlas) Genome Sequencing Centers (GSCs). Data in two formats, whole exome and whole genome is available for every TCGA cancer case sequenced. Non-tumor DNA serves as a control for each submission. Three centers funded by the National Human Genome Research Institute (NHGRI) provide whole genome sequence: The Broad Institute Sequencing Platform, Broad Institute, Cambridge, Mass.; Human Genome Sequencing Center, Baylor College of Medicine, Houston, Tex., and the Genome Institute at Washington University, Washington University School of Medicine, St. Louis, Mo.

If one were to contract with The Broad Institute individually, the Human WES Express (Deep) service offers tumor-normal pairs or somatic mutation analysis that covers 85% of targeted bases at 50x or greater coverage (information accessed Jun. 10, 2016, genomics.broadinstitute.org/products/while-exome-sequencing). Tumor samples can also be sequenced in a CLIA licensed CAP accredited laboratory at the Broad as well. Commercial whole genome and whole exomes sequencing services are provided by Illumina (illumina.com/areas-of-interest/cancer/research.html), which now also offers a Tumor Immunogenicity discovery platform (ngs-immuno-oncology-application-spotlight-1170-2016-005-1.pdf). Other commercial vendors are also available. This information is provided to demonstrate that whole genome and whole exome sequencing services are broadly available in the marketplace, and based on history, the cost and speed of providing these sequences will continue to decrease. The genomic analysis of human tumor samples is a readily provided service, or can be carried out in the laboratory using commercially provided instruments and systems.

Example 2

Next Gen Sequencing of TCRs

The procedure refers to using sequencing techniques to define the full complement of T cell receptors in a biological sample. The material analyzed will include patient tumor, in which case we will be describing the TCRs present in the tumor. In the peripheral blood, we will be describing the common TCRs present, some of which will be tumor specific. Next Gen sequencing allows the frequency of specific TCRs to be quantified. The application of next generation sequencing to identifying specific pairs of TCR alpha and beta chains is a well-established technique in molecular biology (Dash P, Wang G, Thomas P, 2015, Single-cell analysis of T-cell receptor AB repertoire, in Immunosenecense: Methods and Protocols, Shaw A C (ed.), Methods in Molecular Biology, vol. 1343, Springer Science+Business Media, New York).

A multiplicity of approaches have been developed using current techniques of molecular biology, including the continued developments in automated DNA sequencing, to determine the DNA sequences encoding the TCR alpha chain (TCRA) and the TCR beta chain (TCRB). Moreover, a number of techniques have been developed to assign which TCRA is paired with the TCRB in the same T lymphocytes, or population of T cells that arose from a clonal precursor. For example, in 2012 Sun et al., demonstrated the ability to sequence TCR alpha and beta chains at the single-cell level from phenotypically sorted CD8 T cells Sun X, Saito M, Sato Y, et al., 2012, Unbiased analysis of TCRA/B chains at the single-cell level in human CD8+ T-Cell subsets, PLoS ONE 7: e40386.

In 2014 Han et al., demonstrated the sequencing of TCRA and TCRB from T cells, in some cases sorted by their ability to secrete specific cytokine subsets, isolated by the Miltenyi Biotec cytokine capture system (immunomagnetic particles) Han A, Gianville J, Hansmann L, Davis M M, 2014, Linking T-cell receptor sequence to functional phenotype at the single-cell level, Nature Biotechnology 32:684-692.

In a similar manner the sequences encoding the heavy and light chains that comprise the antibody repertoire encoded by B cells have been analyzed by single-cell sequencing methods. DeKosky B, Kojima T, Rodin A, et al., 2015, In-depth determination and analysis of the human paired heavy- and light-chain antibody repertoire, Nature Medicine 21:86-91.

Example 3

Creation of Lentiviral Vectors Expressing the Tumor Mutanome

To confer expression of the mutanome to antigen presenting cells, patient-derived antigen presenting cells, a non-limiting example being dendritic cells, lentiviral vectors (LV) were used to encode the ten (ten is an approximation and the number of LVs can vary from 1 to 100) most predominant mutant proteins present in the mutanome. The LVs can encode a mutanome containing the relevant epitopes or individually clone each mutated gene into a multiplicity of LVs. The DCs can also be transduced with other genes or non-coding RNA to enhance the effect of producing highly functional DCs and/or T cells. Non-limiting examples of such genes or non-coding RNA are IL-2, IL-4, IL-12, IL-17, IL-15, IL-21, IL-7, IL-4, GM-CSF. miR 21, miR221, and miR142-T. They were also transduced with such proteins so that they facilitate monocyte to DC differentiation, and then switch off once differentiation has occurred by using tissue specific promoters and/or tissue specific miRNA, as known in the art.

LV were rapidly generated by the transduction of a producer cell line with a set of plasmids that encode for the constituent genes required to produce a genetic vector. These plasmids are transfected into the producer cell line as a set, in accordance with current regulatory requirements. One of the plasmids transfected encodes the genetic payload of the LV, that is the desired genes to be delivered to the target cell line. Thus, once the tumor mutanome has been defined, and the mutated genes for expression in the antigen presenting cell selected, these genes will be transferred into plasmids encoding one or more of the mutated proteins. LV can accommodate up to 10,000 base pairs. Thus, up to ten genes or individual genes may be encoded by LV. If the allowable packaged gene(s) size is exceeded, then two or more populations of LV are generated to encode the entire set of the mutanome desired. The mutated genes encoding the mutanome are amplified by PCR, or are synthesized directly and appropriate sequences included that allow for rapid cloning into the LV backbone plasmid (the plasmid that encodes the genes of interest). Once LV encoding the desired mutanome genes is produced, it is then used to transduce antigen presenting cells.

Example 4

Creation of Lentiviral Vectors Expressing TCRs

To confer expression of TCR sequences identified by sequencing patient material, LV is used to encode full length TCRA and TCRB chains. These vectors are then used to transduce patient T cells, thus creating multi specific T cells (native and transduced TCRs).

The ability to molecularly clone, sequence, and transfer a human TCR, using a retroviral gene vector into primary human T cells is well established in the field. The transduced T cell gains the ability to target cells using the vector-transferred TCR. If the T cell transduced is clonal, it can be demonstrated that both TCRs, native and transferred, are functional (Retroviral transduction of a T cell receptor specific for an Epstein-Barr virus-encoded peptide, Clinical Immunology, 98:220-228, see also Jurgens, et al., 2006, Transduction of primary lymphocytes with Epstein-Barr virus (EBV) latent membrane protein-specific T-cell receptor induces lysis of virus-infected cells: a novel strategy for the treatment of Hodgkin's disease and nasopharyngeal carcinoma, J Clinical Immunology, 26:22-32).

LVs are created that encode a single or multiple TCRs, for example whose TCRA and TCRB sequences were derived from T cells isolated from an ovarian cancer patient; and use this LV to transduce autologous patient lymphocytes that have been isolated, activated and cultured in vitro. Examples of culture media used include RPMI-1640, or TexMACS, with or without supplementation with human serum or human serum albumin, and supportive cytokines such as IL-2, IL-7, IL-15, IL-21, or a combination thereof. Activation is facilitated by the use of a nanomatrix that has anti-CD3 and anti-CD28 binding properties such as the Mitenyi TransACT system. Cultivation is achieved according to standard techniques in the field (i.e. in tissue culture flasks) or on an automated culturing platform, such as the CliniMACS Prodigy (Miltenyi Biotec). The presence of the new TCR on the surface of the transduced T cell population from the patient can be demonstrated by antibody staining for the specific TCRB that was transferred, or by PCR for those sequences.

This population of activated T cells, now bearing a cloned TCR(s) derived from the patient are then used to recognize cancer antigens expressed by that patient. For example, if the TCR was originally cloned from a T cell derived by the patient that was activated by a dendritic cell expressing antigen X, the transduced T cell population now becomes activated upon co-culture with a tissue matched APC (such as a dendritic cell or B cell) that has been transduced or transfected to express antigen X. Upon transfer of this T cell population into the patient, anti-tumor activity is evidenced.

In another example, the LV encodes an inhibitor for the native TCR, such as an antisense or shRNA that specifically targets the endogenous TCR but not the TCR encoded in the vector, where the encoded TCR is modified to be resistant to the effects of the antisense or shRNA, thereby creating tumor specific T cells that target the antigen(s), but not endogenous TCR. These engineered T cells may have improved properties of safety and efficacy over T cells that also express the endogenous TCR.

In this Example, both TCR and CAR expressing LVs are generated to enable the anti-tumor effects. The TCR and the CAR can be expressed on the same vector or on different vectors. A preferred embodiment is the production of a multiplicity of vector to express desired CARs, TCRs and any other gene or non-coding nucleic acid (collectively referred to as payloads) that could enhance the therapeutic or prophylactic effects of the medicinal product.

Example 5

Creation of Lentiviral Vectors Expressing CARs

A key element is the transduction of patient T cells with chimeric antigen receptors (CARs). The CAR must be expressed on the surface of the T cell to a sufficient level to ensure adequate activation of the transduced T cell upon encountering a CAR target cell. For example, a CD19 CAR-bearing T cell is stimulated by normal B cells expressing CD19 or by leukemias expressing CD19. CARs will not be specific for mutated tumor proteins that have been identified, but will instead target normal B cells or other expendable cell types that may be present in the tumor microenvironment, such myeloid derived suppressor cells (MDSC), tumor associated macrophages (TAM), tumor associated fibroblasts or fibrocytes, or other cell types present in the tumor stroma.

In the case of B cells, the safety profile of CD19- and CD20-specific CARs is well established. A dual CAR that targets both CD19 and CD20 may also be used. It is reactivity to these heterologous, or self-antigens, that will drive expansion of the tumor specific T cells in the body upon infusion, and perhaps also in vitro during culture (for example, if the antigens are shared with dendritic cells). A non-exhaustive list of antigens are as follows: CD19, CD20, CD22, CD33, CD38, CD14, CD11b, TIE-2, VEGFR1, VEGFR2. The DCs can be further engineered for enhancement by expressing genes such as GM-CSF, IL-4, TRP2 and/or IFN-alpha, as non-exhaustive examples, or as described above. The DCs can also be used for infusion into the patient, if desired. In this manner the DC would serve to prime or boost the activity of the transduced T cell population that now expresses the cognate TCR in the body.

One non-limiting example is the inclusion of other elements within the vectors that could better fine tune expression of the payloads to enhance or optimize the desired effect. These include, but are not limited to, genetic switches, suicide genes, rheostat elements and the like. For example, expression of the CARs may be desired for only a period of time after therapy and it may be preferred to switch off CAR expression but maintain TCR expression over longer term in the body so that the engineered T cells can continue to survey the body for tumor cells.

Example 6

Culture of DC and Transduction with Lentiviral Vectors Expressing Mutanome library (DCmutn)

To present mutant proteins to patient T cells, autologous antigen presenting cells, such as dendritic cells (DC), are transduced to express mutant proteins encoded by the mutanome, the specific proteins expressed being defined by the mutant proteins most highly expressed in the tumor. This in vitro procedure allows precise analysis and evaluation of immunotherapeutic T cell populations prior to infusion.

One non-limiting example is the isolation of monocytes from the peripheral blood of patients under non-GMP conditions and first transduce them with a multiplicity of LVs expressing the mutated antigens and then differentiate them to dendritic cells using soluble IL-4 and GM-CSF. Once the cells have been differentiated, patient T cells are subcultured with the dendritic cells to expand tumor specific T cells. The tumor specific T cells are then isolated by a number of methods and the specific TCRs sequenced and determined. These TCRs are then synthesized and cloned into LVs for use in vectors that are manufactured under GMP conditions as the medicinal product.

Another non-limiting example employs the same isolation of monocytes and LV-mediated generation of antigen-specific dendritic cells, but under GMP conditions. The patient T cells are transduced with a LV-anti-CD19 CAR before being cultured with the gene modified DCs for less than 4 days before the antigen-specific T cells, and possibly also the antigen-expressing DCs, are infused back to the patient as the therapeutic medicinal product.

Example 7

Transduction of Patient PBMC with CARs (T-CAR)

To facilitate T cell expansion, and to also escape from tumor suppressive signals in the body, patient T cells are transduced with CARs, such as those targeting CD19, CD20, or other expendable self-antigens. The CARS contain both "signal 1" which, for example, is provided by the CR3 zeta chain (signal 1 refers to that normally invoked by the TCR upon encountering a cognate peptide-MHC complex and includes phosphorylation of the TCR-zeta chain), and "signal 2" which is provided by CD137, CD28, or other T cell signal transducing molecules known to play a role in T cell activation and the induction of T cell expansions and persistence (signal 2 refers to those signal required to biologically allow T cells that have received signal 1 to be further stimulated and persist either in vitro or in vivo and can include activation of the Jak-STAT pathway, PI3 kinase, PKC subtypes, TRAF pathway, or NF-kappaB pathways). Signal 1 and signal 2 can be encoded by the same CAR construct, or can be distributed among different LV-encoded gene products that would serve to activate T cells upon encountering the specific CAR ligand(s). The expression of the CAR construct as a means to ensure persistence of the TCR-transduced patient T cell population is a central aspect of the adoptive immunotherapy described herein, in that the persistence and survival signals for the T cell are provided by the CAR, even if the tumor-specific TCR is insufficient to do so.

Example 8

Transduction of Patient PBMC with TCRs (recT)

LV are generated that express TCRA and TCRB chains identified by sequencing of tumor and peripheral blood. Depending on the number of TCRA and TCRB pairs identified, a LV may encode multiple TCRs, or multiple LV are generated with single TCRs, or a combination of both. Specific techniques to identify pairing of TCRA and TCRB chains, as detailed in the description of DNA sequencing-based TCR identification above, are employed in the design of these vectors. These T cells are reactive to the tumor mutanome as presented by LV transduced DC or B cells or by tumor cells in vivo. Thus, TCR sequences derived from an ovarian cancer patient (either from the peripheral blood or lymphocytes from tumor excision that have been determined to be tumor reactive, for example by the expression of a set of activation markers or by the reactivity to an APC expressing a tumor-encoded protein, i.e. part of the mutantome) is molecularly cloned in to a LV vector, and that vector used to transduce patient T cells, such that the population of T cells transduced now expresses the tumor-reactive TCR. The LV transduced T cell population is tumor reactive, and could be re-infused to the patient.

Example 9

Transduction of Patient PBMC with CAR and TCRs (recT-CAR)

In some cases, patient T cells are transduced both with at least one CAR and a multiplicity of recombinant TCR sequences (recT). These engineered multi-specific T cells are able to react to tumor cells through native TCRs or recT, enhance anti-tumor effect and enable the T cells to persist by virtue of the CAR. In this case a T cell population from a patient with ovarian cancer is transduced with LV vector(s) that encode(s) both a TCR (originally being derived from the patient and determined to be tumor reactive) and a CAR. The TCR serves to activate and direct anti-tumor activity and the CAR serves to enable persistence of the therapeutic T cell population in the body. To construct a case in the singular, the ovarian tumor is sequenced at the genome or exome level, and tumor antigen X identified. The antigen X is then transduced via a LV to be expressed in an autologous APC such as a dendritic cell. Patient lymphocytes are then co-incubated with DC expressing X and reactive cells sequenced to identify TCRA and TCRB sequences. The TCRA and TCRB pairs derived from this sequencing are then used to construct a LV that expresses X-specific TCR (s). Alternatively, tumor antigen-reactive T cells are identified by virtue of other activation markers directly from blood or tumor tissue and TCRA and TCRB sequences identified and cloned into LV. Patient T cells are then activated in culture ex vivo with TrasnAct reagent (which stimulates T cells through CD3 and CD28) in culture media. Activated T cells are then transduced with two separate LV, one encoding the TCR and a second encoding the TCR(s) reactive to X; or, a single vector that co-expresses a CAR and a TCR. The transduced T cell population is then expanded in culture in order to demonstrate expression of the transgenes. Once expression of the LV-encoded sequences is verified, this therapeutic T cell population is infused back into the patient for anti-cancer effect. This approach can be multimerized by increasing X to include a greater number of tumor-associated mutant proteins (mutanome products). This approach can also be multimerized by identifying more than one TCR that is associated with anti-tumor cells or by reactivity to an APC expressing a number of tumor antigens derived from the mutanome. The effector T cell population is then infused into the patient for therapeutic effect, the polyclonal T cell population thus expressing a single TCR specific for X along with a CAR, or polyclonal T cell population expressing a multiplicity of TCRs reactive to a number of cancer antigens, also co-expressed with a CAR. This key inventive step describes a novel effector T cell population derived from the patient that has been engineered to express a CAR against a non-essential antigen encoded by normal tissues, such as CD19 or CD20, and tumor-specific TCRs.

Example 10

Co-Culture of T Cell Populations with Transduced DC

To expand tumor-reactive T cells (regardless of transduction with CAR, recT, CAR and recT), T cells are co-cultured with DC expressing a subset of the tumor mutantome. In one embodiment, recT expressing cells do not require culture on DC as the recT+CAR combination may be sufficient to expand tumor reactive T cells in the body. Co-culture with antigen presenting cells such as DC verifies the tumor reactivity of TCRA and TCRB expression vectors and could be routinely performed as a test. The cells are cultured with a variety of possible cytokines or other factors to enhance the effects of producing or identifying the antigen specific T cells. The APCs or DCs could also be cultured in the presence of factors to further enhance antigen specific T cell expansion. Non-limiting examples are the addition of an anti-PD1 inhibitor, or the addition of IL-12, but there are many possible factors that could be tested and evaluated for their enhancing effects during co-culture.

Example 11

Expansion of RecT-CAR-T Population by Co-Administration or Sequential Administration of Autologous Cell Products Capable of Providing CAR or RecT-Mediated Signaling to the Therapeutic T Cell Population In a variant of this procedure, the LV-mutanome transduced DC (or other APC) and the effector T cell populations may both be infused or injected into the patient. It is also conceived that this second cell population could be cultured for an additional period of time and then infused, or cryo-preserved and then administered at a single or multiple consecutive times. For example, mutanome-expressing DC injected subcutaneously, into a lymph node, or other sites in the body, may enhance the expansion and function of the recT or native anti-tumor TCR that have been injected intravenously. In this scenario, CAR expression drives expansion of the transduced T cell populations upon encountering normal antigen to which the CAR is specific. The introduction of the dendritic cell population expressing mutanome-encoded proteins serves to drive anti-tumor T cell function by virtue of the recT expressed by the T cell population. It also may be that self-antigen driving the CAR, for example CD19, is extinguished to such a degree that it no longer expands the therapeutic T cell population. In this case the autologous APC, for example dendritic cells or cryopreserved B cells, or Epstein-Barr virus immortalized B cells that have been inactivated, may be used to expand the recT-CAR-T population. Furthermore, the immortalized B cell line may also be used to express mutanome proteins.

Immortalization of patient B cells with EBV is a standard service available both in academic laboratories (for example at the University of North Carolina School of Medicine, seeunclineberger.org/research/core-facilities/tissueculture/b-cell-immortalization-services) and as a commercial service (for example see Applied Biologic Material, ABM, Inc., abmgood.com/EBV-Cell-Immortalization.html). Here the patient B cell is exposed to the Epstein-Barr virus (EBV), in a culture supernatant form, and transformed B cell colonies expanded. These patient-derived autologous cells are commonly used in genetics, virological and immunological procedures.

Thus, this ancillary autologous cell product will serve to expand the therapeutic T cell population by virtue of expressing the CAR target as well as the recT target antigen. If the ancillary APC product does not express the CAR target, it will stimulate the therapeutic T cell population by expression of the mutanome proteins alone.

Example 12

Specific Populations of T Cells Created for Immunotherapy

The compositions and methods described here create a number of T cell populations that are suitable for adoptive immunotherapy. In all cases, when the CAR is included, its purpose is not to react to tumor antigens themselves, but rather to drive expansion of patient T cells or to target immunosuppressive cells, either with or without co-expression of recT. These cell populations can be summarized as follows:

A. T-CAR cultured with DCmutn—where the T-CAR is directed to an immunosuppressive cell target and the DCmutn expands antigen specific T cells.

B. recT-CAR, not cultured with DCmutn—where the rec-T-CAR are genetically modified T cells that also express CAR, but the cells themselves were not cultured on DCs. The rec-T TCRs were identified by culturing a separate set of T cells with DCmutn cells.

C. recT-CAR, cultured with DCmutn—where the rec-T CAR cells were generated by transducing patient T cells with a CAR and culturing the cells on DCmutn cells to expand and isolate antigen specific T cells that additionally express a CAR targeted to tumor suppressive cell population and for longevity/expansion of the T cell populations.

D. recT, not cultured with DCmutn—where the rec-T cells are genetically modified T cells that DO NOT express CAR, and the cells themselves were not cultured on DCs. The rec-T TCRs were identified by culturing a separate set of T cells with DCmutn cells.

E. recT, cultured with DCmutn—where the rec-T cells are cultured with DCmutn cells to obtain TCR antigen specific T cells.

F. a DC-mutanome population used in vitro, and may also serve as an in vivo adjuvant/vaccine—where the DC-mutanome population is used as a vaccine to drive expansion of rec-T or rec-T CAR cells in the body.

Example 13

Alternate Donor and T Cell Types

Two important variants of the adoptive immunotherapy procedure described herein may be considered with respect to alternate donor and T cell types.

The first variation is adoptive immunotherapy in the context of hematopoietic stem cell transplantation (HSCT). HSCT has been attempted in both hematologic malignancies and for solid tumors. For application of the procedures described here post-HSCT, the DC (or other APC) and T cell populations are derived from the bone marrow (HSC) donor, and therapeutic T cells generated, infused post-HSCT.

Thus a patient with, for example, myeloma, has their malignancy sequenced and the mutanome defined. Mutanome protein antigens are expressed in APCs from the HSC donor (by virtue of LV transduction). HSC Donor-derived T cells are activated and selected for direct use, or for TCR sequencing, following co-culture with APC that express mutanome-encoded proteins. The CAR construct remains the same, as for non-HSCT applications of the technology, as it is reactive to a normal self-antigen.

The second variation is the use of alternate T cell populations for adoptive immunotherapy. It is well established that cell surface activation markers, such as CD137, CD69, PD-1, CD25, class II MHC, and others are often used to define and isolate activated T cell populations (for example using the Miltenyi Biotec CliniMACS CD137-Biotin reagent or the CliniMACS CD25 Reagent). Activated T cell populations are isolated from the peripheral blood, from tumor, or upon exposure to dendritic cells expressing tumor associated antigens (DCmutn) using these methods. Similarly, the ability to isolate activated T lymphocytes that produce activation-associated cytokines can be used as a means to isolate tumor antigen reactive T cells (for example using the Miltenyi Biotec CliniMACS Cytokine Capture System (IFN-gamma)). Effector T cell populations are also sorted into specific cell populations using magnetic bead sorting, flow cytometry, solid-phase antibody bound to a plastic surface, solid-phase bound ligand to the desired marker expressed by the T cell type desired adhered to a matrix, etc., in a manner whereby said T cell types are defined by the expression of cell surface proteins (markers). For example, CD4 cells that are reactive to mutant peptide bound by class II MHC or CD8 cells that are reactive to mutant peptide bound to class I MHC can be isolated using CD4 or CD8 immunomagnetic beads (for example, using the Miltenyi Biotec CliniMACS CD4 reagent or the CliniMACS CD8 Reagent). These cell types are then used as a single population (CD4 only, for example), or in specific combinations or ratios. Similarly, markers of T cell differentiation have been used to select specific populations for adoptive immunotherapy. These differentiation markers are be used to positively or negatively select memory T cell populations or naïve T cell populations (for example using the CliniMACS CD45RA reagent or the CliniMACS CD62L Reagent). Furthermore, specific physiological aspects of T cell populations could be used to identify more primitive T cell populations that may expand better in vivo (for example using the reagents that identify cell populations that express the enzyme aldehyde dehydrogenase or expression of specific combinations of sodium (Na+) and potassium channels (K+) on the T cell surface, see Liepins A, et al., 1989, "Serotonin modulated Ca++ dependent K+ channels in alloimmune effector cell lytic function. Immunopharmacol Immunotoxicol 11:165-178, and Gallin E K, 1986, Ionic channels in leukocytes, J Leukoc Bio 39:241-254). Thus, in the above example, either prior to culture of T cells derived from a myeloma patient with APC (DCmutn), or after exposure of an unselected T cell population to the APC, but prior to infusion in the patient, T cell subsets are isolated as a therapeutic cell population. In one application these markers or physiological characteristics are used to more accurately identify tumor-reactive T cells and thus serve as the basis of more efficient identification of TCRA and TCRB sequence. In another application, the T cell population used for immunotherapy is preselected for certain markers prior to infusion in the patient, but after the induced expression or recTCR and CAR via LV transduction. In another application, T cells that express tumor-reactive markers are selected following isolation from the patient, and this selected subset co-cultured with APC (DCmutn) in order to more efficiently identify tumor-specific TCRA and RCRB sequence.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

REFERENCE TO THE SEQUENCE LISTING

This application contains a Sequence Listing electronically to be submitted to the United States Patent and Trademark Receiving Office via a PDF file entitled "Sequence Listing". The Sequence Listing is incorporated by reference.

SEQUENCES OF THE DISCLOSURE

The nucleic and amino acid sequences listed below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

```
SEQ ID NO: 1 is the nucleotide sequence of leader/signal peptide sequence:
atgctgctgctggtgaccagcctgctgctgtgcgaactgccgcatccggcgtttctgctgattccg SEQ ID NO: 2 is the amino acid sequence of leader/signal peptide sequence:
MLLLVTSLLLCELPHPAFLLIP SEQ ID NO.: 3 is the nucleotide sequence of DNA CD8 transmembrane domain:
atctacatct gggcgccctt ggccgggact tgtgggtcc ttctcctgtc actggttatc accctttact gc SEQ ID NO. 4 is the amino acid sequence of CD8 transmembrane domain:
Ile Trp Ala Pro Leu Ala Gly Thr Cys Gly Val Leu Leu Leu Ser Leu Val Ile Thr Leu Tyr Cys SEQ ID NO: 5 is the nucleotide sequence of DNA CD8 hinge domain:
accacgacgc cagcgccgcg accaccaaca ccggcgccca ccatcgcgtc gcagcccctg tccctgcgcc cagaggcgtg ccggccagcg gcggggggcg cagtgcacac gagggggctg gacttcgcct gtgat SEQ ID NO: 6 is the amino acid sequence of CD8 hinge domain:
Thr Thr Thr Pro Ala Pro Arg Pro Pro Thr Pro Ala Pro Thr Ile Ala
```

Ser Gln Pro Leu Ser Leu Arg Pro Glu Ala Cys Arg Pro Ala Ala Gly

Gly Ala Val His Thr Arg Gly Leu Asp Phe Ala Cys Asp Ile Tyr

SEQ ID NO: 7 is the amino acid sequence of amino acid numbers 118 to 178 hinge region of CD8.alpha. (NCBI RefSeq: NP.sub.--001759.3):
Lys Arg Gly Arg Lys Lys Leu Leu Tyr Ile Phe Lys Gln Pro Phe Met Arg Pro Val Gln Thr Thr Gln Glu Glu Asp Gly Cys Ser Cys Arg Phe Pro Glu Glu Glu Glu Gly Gly Cys Glu Leu SEQ ID NO: 8 is the amino acid sequence of Human IgG CL sequence:
Gly Gln Pro Lys Ala Ala Pro Ser Val Thr Leu Phe Pro Pro Ser Ser Glu Glu Leu Gln Ala Asn Lys Ala Thr Leu Val Cys Leu Ile Ser Asp Phe Tyr Pro Gly Ala Val Thr Val Ala Trp Lys Ala Asp Ser Ser Pro Val Lys Ala Gly Val Glu Thr Thr Thr Pro Ser Lys Gln Ser Asn Asn Lys Tyr Ala Ala Ser Ser Tyr Leu Ser Leu Thr Pro Glu Gln Trp Lys Ser His Arg Ser Tyr Ser Cys Gln Val Thr His Glu Gly Ser Thr Val Glu Lys Thr Val Ala Pro Thr Glu Cys Ser SEQ ID NO 9 is the nucleotide sequence of DNA signaling domain of 4-1BB:
aaacggggca gaaagaaact cctgtatata ttcaaacaac catttatgag accagtacaa actactcaag aggaagatgg ctgtagctgc cgatttccag aagaagaaga aggaggatgt gaactg SEQ ID NO: 10 is the amino acid sequence of signaling domain of 4-1BB:
Lys Arg Gly Arg Lys Lys Leu Leu Tyr Ile Phe Lys Gln Pro Phe Met Arg Pro Val Gln Thr Thr Gln Glu Glu Asp Gly Cys Ser Cys Arg Phe Pro Glu Glu Glu Glu Gly Gly Cys Glu Leu SEQ ID NO: 11 is the nucleotide sequence of DNA signaling domain of CD3-zeta:
agagtgaagt tcagcaggag cgcagacgcc cccgcgtaca agcagggcca gaaccagctc tataacgagc tcaatctagg acgaagagag gagtacgatg ttttggacaa gagacgtggc cgggaccctg agatgggggg aaagccgaga aggaagaacc ctcaggaagg cctgtacaat gaactgcaga agataagat ggcggaggcc tacagtgaga ttgggatgaa aggcgagcgc cggaggggca aggggcacga tggcctttac cagggtctca gtacagccac caaggacacc tacgacgccc ttcacatgca ggccctgccc cctcgc SEQ ID NO: 12 is the amino acid sequence of CD3zeta:
Arg Val Lys Phe Ser Arg Ser Ala Asp Ala Pro Ala Tyr Lys Gln Gly Gln Asn Gln Leu Tyr Asn Glu Leu Asn Leu Gly Arg Arg Glu Glu Tyr Asp Val Leu Asp Lys Arg Arg Gly Arg Asp Pro Glu Met Gly Gly Lys Pro Arg Arg Lys Asn Pro Gln Glu Gly Leu Tyr Asn Glu Leu Gln Lys Asp Lys Met Ala Glu Ala Tyr Ser Glu Ile Gly Met Lys Gly Glu Arg Arg Arg Gly Lys Gly His Asp Gly Leu Tyr Gln Gly Leu Ser Thr Ala Thr Lys Asp Thr Tyr Asp Ala Leu His Met Gln Ala Leu Pro Pro Arg SEQ ID NO: 13 is the nucleotide sequence of Nucleic acid sequence (DNA) SP-CD19binder-CD8link-CD4tm-signals LTG1562:
atgctgctgctggtgaccagcctgctgctgtgcgaactgccgcatccggcgtttctgctg attccggatattcagatgacccagaccaccagcagcctgagcgcgagcctgggcgatcgc gtgaccattagctgccgcgcgagccaggatattagcaaatatctgaactggtatcagcag aaaccggatggcaccgtgaaactgctgatttatcataccagccgcctgcatagcggcgtg ccgagccgctttagcggcagcggcagcggcaccgattatagcctgaccattagcaacctg -continued

```
gaacaggaagatattgcgacctattttttgccagcagggcaacaccctgccgtatacctttt ggcggcggcaccaaactggaaattaccggcggcggcggcagcggcggcggcggcagcggc ggcggcggcagcgaagtgaaactgcaggaaagcggcccgggcctggtggcgccgagccag agcctgagcgtgacctgcaccgtgagcggcgtgagcctgccggattatggcgtgagctgg attcgccagccgccgcgcaaaggcctggaatggctgggcgtgatttggggcagcgaaacc acctattataacagcgcgctgaaaagccgcctgaccattattaaagataacagcaaaagc caggtgtttctgaaaatgaacagcctgcagaccgatgataccgcgatttattattgcgcg aaacattattattatggcggcagctatgcgatggattattggggccagggcaccagcgtg accgtgagcagcgcggcggcgccggcgccgcgcccgccgaccccggcgccgaccattgcg agccagccgctgagcctgcgccccggaagcgtgccgcccggcggcggggcggcgcggtgcat acccgcggcctggattttgtgcagccgatggcgctgattgtgctgggcggcgtggcgggc ctgctgctgtttattggcctgggcattttttttttgcgtgcgctgccgcccgcgccgcaaa aaactgc tgtatatttttaaacagccgtttatgcgcccggtgcagaccacccaggaagaa gatggctgcagc tgccgctttccggaagaagaagaaggcggctgcgaactgcgcgtgaaa tttagccgcagcgc ggatgcgccggcgtatcagcagggccagaaccagctgtataacgaa ctgaacctgggccgcc gcgaagaatatgatgtgctggataaacgccgcggccgcgatccg gaaatgggcggcaaacc gcgccgcaaaaacccgcaggaaggcctgtataacgaactgcag aaagataaaatggcggaa gcgtatagcgaaattggcatgaaaggcgaacgccgccgcggc aaaggccatgatggcctgtat cagggcctgagcaccgcgaccaaagatacctatgatgcg ctgcatatgcaggcgctgccgccgcgc
```

SEQ ID NO: 14 is the amino acid sequence of SP-CD19binder-CD8link-CD4tm-signals LTG1562:

<u>MLLLVTSLLLCELPHPAFLLIP</u>DIQMTQTTSSLSASLGD

RVTISCRASQDISKYLNWYQQKPDGTVKLLIYHTSRLHSGVPSRFSGSGS

GTDYSLTISNLEQEDIATYFCQQGNTLPYTFGGGTKLEITGGGGSGGGGS

GGGGSEVKLQESGPGLVAPSQSLSVTCTVSGVSLPDYGVSWIRQPPRKGL

EWLGVIWGSETTYYNSALKSRLTIIKDNSKSQVFLKMNSLQTDDTAIYYC

AKHYYYGGSYAMDYWGQGTSVTVSSAAAPAPRPPTPAPTIASQPLSLRPE

ACRPAAGGAVHTRGLDF<u>VQPMALIVLGGVAGLLLFIGLGIFFCVRCR</u>PRR

KKLLYIFKQPFMRPVQTTQEEDGCSCRFPEEEEGGCELRVKFSRSADAPA

YQQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPR

SEQ ID NO: 15 is the nucleotide sequence of Scvf cd 19:

```
gacatccaga tgacacagac tacatcctcc ctgtctgcct ctctgggaga cagagtcacc atcagttgca gggcaagtca ggacattagt aaatatttaa attggtatca gcagaaacca gatggaactg ttaaactcct gatctaccat acatcaagat tacactcagg agtcccatca aggttcagtg gcagtgggtc tggaacagat tattctctca ccattagcaa cctggagcaa gaagatattg ccacttactt ttgccaacag gtaatacgc ttccgtacac gttcggaggg gggaccaagc tggagatcac aggtggcggt ggctcgggcg gtggtgggtc gggtggcggc ggatctgagg tgaaactgca ggagtcagga cctggcctgg tggcgccctc acagagcctg tccgtcacat gcactgtctc aggggtctca ttacccgact atggtgtaag ctggattcgc cagcctccac gaagggtct ggagtggctg ggagtaatat ggggtagtga aaccacatac tataattcag ctctcaaatc cagactgacc atcatcaagg acaactccaa gagccaagtt ttcttaaaaa tgaacagtct gcaaactgat gacacagcca tttactactg tgccaaacat tattactacg gtggtagcta tgctatggac tactgggggcc aaggaacctc agtcaccgtc tcctca
```

SEQ ID NO: 16 is the amino acid sequence of Scvf cd 19:
Asp Ile Gln Met Thr Gln Thr Thr Ser Ser Leu Ser Ala Ser Leu Gly Asp Arg Val Thr Ile Ser Cys Arg Ala Ser Gln Asp Ile Ser Lys Tyr Leu Asn Trp Tyr Gln Gln Lys Pro Asp Gly Thr Val Lys Leu Leu Ile Tyr His Thr Ser Arg Leu His Ser Gly Val Pro Ser Arg Phe Ser Gly Ser Gly Ser Gly Thr Asp Tyr Ser Leu Thr Ile Ser Asn Leu Glu Gln Glu Asp Ile Ala Thr Tyr Phe Cys Gln Gln Gly Asn Thr Leu Pro Tyr Thr Phe Gly Gly Gly Thr Lys Leu Glu Ile Thr Gly Gly Gly Gly Ser 100 105 110 Gly Gly Gly Gly Ser Gly Gly Gly Gly Ser Glu Val Lys Leu Gln Glu Ser Gly Pro Gly Leu Val Ala Pro Ser Gln Ser Leu Ser Val Thr Cys Thr Val Ser Gly Val Ser Leu Pro Asp Tyr Gly Val Ser Trp Ile Arg Gln Pro Pro Arg Lys Gly Leu Glu Trp Leu Gly Val Ile Trp Gly Ser Glu Thr Thr Tyr Tyr Asn Ser Ala Leu Lys Ser Arg Leu Thr Ile Ile Lys Asp Asn Ser Lys Ser Gln Val Phe Leu Lys Met Asn Ser Leu Gln Thr Asp Asp Thr Ala Ile Tyr Tyr Cys Ala Lys His Tyr Tyr Tyr Gly Gly Ser Tyr Ala Met Asp Tyr Trp Gly Gln Gly Thr Ser Val Thr Val Ser Ser SEQ ID NO: 17 is the nucleotide sequence of SP-CD19binder-CD8link-CD8tm-signaling LTG1494 (c.f., FIG. 3A, Applicant's co-pending Provisional Patent Application No. 62/239,509):
atgctgctgctggtgaccagcctgctgctgtgcgaactgccgcatccggcgtttctgctg attccggataccgatattcagatgacccagaccaccagcagcctgagcgcgagcctgggc gatcgcgtgaccattagctgccgcgcgagccaggatattagcaaatatctgaactggtat cagcagaaaccggatggcaccgtgaaactgctgatttatcataccagccgcctgcatagc ggcgtgccgagccgctttagcggcagcggcagcggcaccgattatagcctgaccattagc aacctggaacaggaagatattgcgacctattttttgccagcagggcaacaccctgccgtat accatggcggcggcaccaaactggaaattaccggcagcaccagcggcagcggcaaaccg ggcagcggcgaaggcagcaccaaaggcgaagtgaaactgcaggaaagcggcccgggcctg gtggcgccgagccagagcctgagcgtgacctgcaccgtgagcggcgtgagcctgccggat tatggcgtgagctggattcgccagccgccgcgcaaaggcctggaatggctgggcgtgatt tggggcagcgaaaccacctattataacagcgcgctgaaaagccgcctgaccattattaaa gataacagcaaaagccaggtgtttctgaaaatgaacagcctgcagaccgatgataccgcg atttattattgcgcgaaacattattattatggcggcagctatgcgatggattattgggggc cagggcaccagcgtgaccgtgagcagcgcggcggcgaccaccaccccggcgccgcgcccg ccgaccccggcgccgaccattgcgagccagccgctgagcctgcgcccggaagcgtgccgc ccggcggagggcggcgcggtgcatacccgcggcctggattttgcgtgcgatatttatatt tgggcgccgctggcgggcacctgcggcgtgctgctgctgagcctggtgattaccctgtat tgcaaacgcggccgcaaaaaactgctgtatatttttaaacagccgtttatgcgcccggtg cagaccacccaggaagaagatggctgcagctgccgctttccggaagaagaagaaggcggc tgcgaactgcgcgtgaaatttagccgcagcgcggatgcgccggcgtatcagcagggccag aaccagctgtataacgaactgaacctgggccgccgcgaagaatatgatgtgctggataaa cgccgcggccgcgatccggaaatgggcggcaaaccgcgccgcaaaaacccgcaggaaggc ctgtataacgaactgcagaaagataaaatggcggaagcgtatagcgaaattggcatgaaa ggcgaacgccgccgcggcaaaggccatgatggcctgtatcagggcctgagcaccgcgacc aaagataccatgatgcgctgcatatgcaggcgctgccgccgcgc SEQ ID NO: 18 is the amino acid sequence of SP-CD19binder-CD8link-CD8tm-signaling LTG1494 (c.f., FIG. 3A, Applicant's co-pending Provisional Patent Application No. 62/239,509):

*MILLVTSLLICELPHPAFLLI*PDTDIQMTQTTSSLSASLGD

*RVTISCRASQDISKYLNWYQQKPDGTVKLLIYHTSRLHSGVPSRFSGSGS*

*GTDYSLTISNLEQEDIATYFCQQGNTLPYTFGGGTKLEITGSTSGSGKPG*

*SGEGSTKGEVKLQESGPGLVAPSQSLSVTCTVSGVSLPDYGVSWIRQPPR*

*KGLEWLGVIWGSETTYYNSALKSRLTIIKDNSKSQVFLKMNSLQTDDTAIYYC*

*AKHYYYGGSYAMDYWGQGTSVTVSS*AAATTT**PAPRPPTPAPTIASQPLSRPE*

ACRPAAGGAVHTRGLDF<u>ACDIYIWAPLAGTCGVLLLSLVITLYCK</u>RGRKKLLY

IFKQPFMRPVQTTQEEDGCSCRFPEEEEGGCELRVKFSRSADAPAYQQGQNQL

YNELNLGRREEYDVLDKRRGRDPEMGGKPRRKNPQEGLYNELQKDKMAEAYSE

IGMKGERRRGKGHDGLYQGLSTATKDTYDALHMQALPPR

SEQ ID NO: 19 is the nucleotide sequence of SP-CD19binder-CD8link-CD8tm-signals (LTI re-engineered) (LTG1538) (c.f., FIG. 3B of Applicant's co-pending Provisional Patent Application No. 62/239,509):
atgctgctgctggtgaccagcctgctgctgtgcgaactgccgcatccggcgtttctgctg attccggatattcagatgacccagaccaccagcagcctgagcgcgagcctgggcgatcgc gtgaccattagctgccgcgcgagccaggatattagcaaatatctgaactggtatcagcag aaaccggatggcaccgtgaaactgctgatttatcataccagccgcctgcatagcggcgtg ccgagccgctttagcggcagcggcagcggcaccgattatagcctgaccattagcaacctg gaacaggaagatattgcgacctatttttgccagcagggcaacaccctgccgtataccttt ggcggcggcaccaaactggaaattaccggcggcggcggcagcggcggcggcggcagcggc ggcggcggcagcgaagtgaaactgcaggaaagcggcccgggcctggtggcgccgagccag agcctgagcgtgacctgcaccgtgagcggcgtgagcctgccggattatggcgtgagctgg attcgccagccgccgcgcaaaggcctggaatggctgggcgtgatttggggcagcgaaacc acctattataacagcgcgctgaaaagccgcctgaccattattaaagataacagcaaaagc caggtgtttctgaaaatgaacagcctgcagaccgatgataccgcgatttattattgcgcg aaacattattattatggcggcagctatgcgatggattattggggccagggcaccagcgtg accgtgagcagcgcggcggcgaccaccaccccggcgccgcgcccgccgaccccggcgccg accattgcgagccagccgctgagcctgcgcccggaagcgtgccgcccggcggcgggcggc gcggtgcatacccgcggcctggattttgcgtgcgatatttatatttgggcgccgctggcg ggcacctgcggcgtgctgctgctgagcctggtgattaccctgtattgcaaacgcggccgc aaaaaactgctgtatattataaacagccgtttatgcgcccggtgcagaccacccaggaa gaagatggctgcagctgccgattccggaagaagaagaaggcggctgcgaactgcgcgtg aaatttagccgcagcgcggatgcgccggcgtatcagcagggccagaaccagctgtataac gaactgaacctgggccgccgcgaagaatatgatgtgctggataaacgccgcggccgcgat ccggaaatgggcggcaaaccgcgccgcaaaaacccgcaggaaggcctgtataacgaactg cagaaagataaaatggcggaagcgtatagcgaaattggcatgaaaggcgaacgccgccgc ggcaaaggccatgatggcctgtatcagggcctgagcaccgcgaccaaagatacctatgat gcgctgcatatgcaggcgctgccgccgcgc SEQ ID NO: 20 is the amino acid sequence of SP-CD19binder-CD8link-CD8tm-signals (LTI re-engineered) (LTG1538) (c.f., FIG. 3B of Applicant's co-pending Provisional Patent Application No. 62/239,509):
*MILLVTSLLICELPHPAFLLI*PDIQMTQTTSSLSASLGD

*RVTISCRASQDISKYLNWYQQKPDGTVKLLIYHTSRLHSGVPSRFSGSGS*

*GTDYSLTISNLEQEDIATYFCQQGNTLPYTFGGGTKLEITGGGGSGGGGS*

*GGGGSEVKLQESGPGLVAPSQSLSVTCTVSGVSLPDYGVSWIRQPPRKGL*

*EWLGVIWGSETTYYNSALKSRLTIIKDNSKSQVFLKMNSLQTDDTAIYYC*

*AKHYYYGGSYAMDYWGQGTSVTVSS*AAATTTPAPRPPTPAPTIASQPLSLRPE

ACRPAAGGAVHTRGLDF<u>ACDIYIWAPLAGTCGVLLLSLVITLYCKR</u>GRKKLLY

IFKQPFMRPVQTTQEEDGCSCRFPEEEEGGCELRVKFSRSADAPAYQQGQNQL

YNELNLGRREEYDVLDKRRGRDPEMGGKPRRKNPQEGLYNELQKDKMAEAYSE

IGMKGERRRGKGHDGLYQGLSTATKDTYDALHMQALPPR

---

What is claimed is:

1. A method of treating a human patient having a solid tumor expressing CD19, the method comprising administering to the patient a pharmaceutical composition comprising an anti-tumor effective amount of an autologous T-cell population transduced with one or more lentiviral vectors encoding single or multiple chimeric antigen receptors (CARs), the single or multiple CARs comprising an isolated nucleic acid sequence selected from the group consisting of SEQ ID NO: 13, SEQ ID NO: 17, and SEQ ID NO: 21 to promote in vivo expansion and persistence of the autologous patient-specific anti-tumor T-cells, wherein the T-cells are co-cultured with autologous dendrite cells differentiated from monocytes, the autologous dendrite cells being transduced with one or more lentiviral vectors expressing patient-derived tumor antigens, wherein the T-cell population is additionally transduced with one or more lentiviral vectors encoding tumor-specific T-cell receptors (TCRs) thereby generating an active patient-specific autologous anti-tumor T-cell population capable of recognizing patient-derived tumor antigens which can be infused directly back into the patient to result in tumor stabilization, tumor reduction, elimination of cancer, or remission of cancer in a patient-specific manner.

2. A method of treating a human patient having a solid tumor the method comprising administering to the patient a pharmaceutical composition comprising an anti-tumor effective amount of an autologous T-cell population transduced with one or more lentiviral vectors encoding single or multiple chimeric antigen receptors (CARs), the single or multiple CARs comprising an anti-CD19, an anti-CD20, or an anti-CD22 antibody or binding fragment thereof, wherein the anti-CD19 CAR comprises an isolated nucleic acid sequence selected from the group consisting of SEQ ID NO: 13, SEQ ID NO: 17, and SEQ ID NO: 21, wherein the T-cell population is additionally transduced with one or more lentiviral vectors encoding tumor-specific T-cell receptors (TCRs) to generate an active patient-specific autologous anti-tumor T-cell population capable of recognizing patient-derived CD19, CD20, or CD22 tumor antigens which can be infused directly back into the patient to promote in vivo expansion, persistence of patient-specific anti-tumor T-cells resulting in tumor stabilization, tumor reduction, elimination of cancer, or remission of cancer in a patient-specific manner.

3. The method of claim 1, wherein the T cell has been preselected by virtue of expressing specific activation or memory-associated surface markers.

4. The method of claim 1, wherein the T cell and dendritic cells are derived from a hematopoietic stem cell donor, and wherein the procedure is carried out in the context of hematopoietic stem cell transplantation.

5. The method of claim 2, wherein the T cell has been preselected by virtue of expressing specific activation or memory-associated surface markers.

6. The method of claim 2, wherein the T cell and dendritic cells are derived from a hematopoietic stem cell donor, and wherein the procedure is carried out in the context of hematopoietic stem cell transplantation.

* * * * *

UNITED STATES PATENT AND TRADEMARK OFFICE
CERTIFICATE OF CORRECTION

PATENT NO. : 10,639,329 B2
APPLICATION NO. : 15/735921
DATED : May 5, 2020
INVENTOR(S) : Boro Dropulic et al.

Page 1 of 1

It is certified that error appears in the above-identified patent and that said Letters Patent is hereby corrected as shown below:

On the Title Page

Item (56) Column 2, Line 5, delete "next-generaton" and insert -- next-generation --.

Item (56) Column 2, Line 6, delete "I-cell function." and insert -- T-cell function. --.

Signed and Sealed this
Seventeenth Day of November, 2020

Andrei Iancu
*Director of the United States Patent and Trademark Office*

SEQUENCE LISTING

<160> NUMBER OF SEQ ID NOS: 21

<210> SEQ ID NO 1
<211> LENGTH: 66
<212> TYPE: DNA
<213> ORGANISM: Artificial Sequence
<220> FEATURE:
<223> OTHER INFORMATION: leader/signal peptide

<400> SEQUENCE: 1
atgctgctgc tggtgaccag cctgctgctg tgcgaactgc cgcatccggc gtttctgctg    60
attccg                                                              66

<210> SEQ ID NO 2
<211> LENGTH: 22
<212> TYPE: PRT
<213> ORGANISM: Artificial Sequence
<220> FEATURE:
<223> OTHER INFORMATION: leader/signal peptide

<400> SEQUENCE: 2

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 3
<211> LENGTH: 72
<212> TYPE: DNA
<213> ORGANISM: Artificial Sequence
<220> FEATURE:
<223> OTHER INFORMATION: CD8 transmembrane domain

<400> SEQUENCE: 3
atctacatct gggcgccctt ggccgggact tgtggggtcc ttctcctgtc actggttatc    60 acccttact gc                                                        72

<210> SEQ ID NO 4
<211> LENGTH: 22
<212> TYPE: PRT
<213> ORGANISM: Artificial Sequence
<220> FEATURE:
<223> OTHER INFORMATION: CD8 transmembrane domain

<400> SEQUENCE: 4

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 5
<211> LENGTH: 135
<212> TYPE: DNA
<213> ORGANISM: Artificial Sequence
<220> FEATURE:
<223> OTHER INFORMATION: CD8 hinge domain

<400> SEQUENCE: 5

```
accacgacgc cagcgccgcg accaccaaca ccggcgccca ccatcgcgtc gcagcccctg      60
tccctgcgcc agaggcgtg ccggccagcg gcggggggcg cagtgcacac gagggggctg     120
gacttcgcct gtgat                                                     135
```

<210> SEQ ID NO 6
<211> LENGTH: 47
<212> TYPE: PRT
<213> ORGANISM: Artificial Sequence
<220> FEATURE:
<223> OTHER INFORMATION: CD8 hinge domain

<400> SEQUENCE: 6

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45
```

<210> SEQ ID NO 7
<211> LENGTH: 42
<212> TYPE: PRT
<213> ORGANISM: Artificial Sequence
<220> FEATURE:
<223> OTHER INFORMATION: amino acid residues 118-178 of CD8.alpha. hinge
      region

<400> SEQUENCE: 7

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40
```

<210> SEQ ID NO 8
<211> LENGTH: 106
<212> TYPE: PRT
<213> ORGANISM: Homo sapiens
<220> FEATURE:
<221> NAME/KEY: MISC_FEATURE
<223> OTHER INFORMATION: IgGCL region

<400> SEQUENCE: 8

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60
```

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 9
<211> LENGTH: 126
<212> TYPE: DNA
<213> ORGANISM: Artificial Sequence
<220> FEATURE:
<223> OTHER INFORMATION: signaling domain of 4-1BB

<400> SEQUENCE: 9
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126

<210> SEQ ID NO 10
<211> LENGTH: 42
<212> TYPE: PRT
<213> ORGANISM: Artificial Sequence
<220> FEATURE:
<223> OTHER INFORMATION: signaling domain of 4-1BB

<400> SEQUENCE: 10

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 11
<211> LENGTH: 336
<212> TYPE: DNA
<213> ORGANISM: Artificial Sequence
<220> FEATURE:
<223> OTHER INFORMATION: signaling domain of CD3-zeta

<400> SEQUENCE: 11
agagtgaagt tcagcaggag cgcagacgcc cccgcgtaca gcagggccca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagatg gcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                            336

<210> SEQ ID NO 12
<211> LENGTH: 112
<212> TYPE: PRT
<213> ORGANISM: Artificial Sequence
<220> FEATURE:
<223> OTHER INFORMATION: CD3zeta

<400> SEQUENCE: 12

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Tyr
              20                  25                  30

Asp Val Leu Asp Lys Arg Gly Arg Asp Pro Glu Met Gly Gly Lys
          35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                  85                  90                  95

Thr Lys Asp Thr Tyr Asp Ala Leu His Met Gln Ala Leu Pro Pro Arg
              100                 105                 110

<210> SEQ ID NO 13
<211> LENGTH: 1467
<212> TYPE: DNA
<213> ORGANISM: Artificial Sequence
<220> FEATURE:
<223> OTHER INFORMATION: SPCD19binder-CD8link-CD4tm-signals LTG 1562

<400> SEQUENCE: 13

| | |
|---|---:|
| atgctgctgc tggtgaccag cctgctgctg tgcgaactgc cgcatccggc gtttctgctg | 60 |
| attccggata ttcagatgac ccagaccacc agcagcctga gcgcgagcct gggcgatcgc | 120 |
| gtgaccatta gctgccgcgc gagccaggat attagcaaat atctgaactg gtatcagcag | 180 |
| aaaccggatg gcaccgtgaa actgctgatt tatcatacca gccgcctgca tagcggcgtg | 240 |
| ccgagccgct ttagcggcag cggcagcggc accgattata gcctgaccat tagcaacctg | 300 |
| gaacaggaag atattgcgac ctattttttgc cagcagggca caccctgcc gtatacccttt | 360 |
| ggcggcggca ccaaactgga aattaccggc ggcggcggca gcggcggcgg cggcagcggc | 420 |
| ggcggcggca gcgaagtgaa actgcaggaa agcggcccgg gcctggtggc gccgagccag | 480 |
| agcctgagcg tgacctgcac cgtgagcggc gtgagcctgc cggattatgg cgtgagctgg | 540 |
| attcgccagc cgccgcgcaa aggcctggaa tggctgggcg tgatttgggg cagcgaaacc | 600 |
| acctattata acagcgcgct gaaaagccgc ctgaccatta ttaaagataa cagcaaaagc | 660 |
| caggtgtttc tgaaaatgaa cagcctgcag accgatgata ccgcgattta ttattgcgcg | 720 |
| aaacattatt attatggcgg cagctatgcg atggattatt ggggccaggg caccagcgtg | 780 |
| accgtgagca gcgcggcggc gccggcgccg cgcccgccga ccccggcgcc gaccattgcg | 840 |
| agccagccgc tgagcctgcg cccggaagcg tgccgcccgg cggcgggcgg cgcggtgcat | 900 |
| acccgcggcc tggattttgt gcagccgatg gcgctgattg tgctgggcgg cgtggcgggc | 960 |
| ctgctgctgt ttattggcct gggcattttt ttttgcgtgc gctgccgccc cgccgcaaa | 1020 |
| aaactgctgt atatttttaa acagccgttt atgcgcccgg tgcagaccac ccaggaagaa | 1080 |
| gatggctgca gctgccgctt tccggaagaa gaagaaggcg gctgcgaact gcgcgtgaaa | 1140 |
| tttagccgca gcgcggatgc gccggcgtat cagcagggcc agaaccagct gtataacgaa | 1200 |
| ctgaacctgg gccgccgcga agaatatgat gtgctggata acgccgcgg ccgcgatccg | 1260 |
| gaaatgggcg gcaaaccgcg ccgcaaaaac ccgcaggaag gcctgtataa cgaactgcag | 1320 |
| aaagataaaa tggcggaagc gtatagcgaa attggcatga aaggcgaacg ccgccgcggc | 1380 |
| aaaggccatg atggcctgta tcagggcctg agcaccgcga ccaaagatac ctatgatgcg | 1440 |
| ctgcatatgc aggcgctgcc gccgcgc | 1467 |

<210> SEQ ID NO 14
<211> LENGTH: 485
<212> TYPE: PRT
<213> ORGANISM: Artificial Sequence
<220> FEATURE:
<223> OTHER INFORMATION: SP-CD19binder-CD8link-CD4tm-signals LTG1562

<400> SEQUENCE: 14

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Val Gln Pro Met Ala Leu Ile Val Leu Gly Gly Val Ala Gly
305                 310                 315                 320

Leu Leu Leu Phe Ile Gly Leu Gly Ile Phe Phe Cys Val Arg Cys Arg
                325                 330                 335

Pro Arg Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
```

```
                370               375               380
Ala Asp Ala Pro Ala Tyr Gln Gln Gly Gln Asn Gln Leu Tyr Asn Glu
385                 390               395                 400

Leu Asn Leu Gly Arg Arg Glu Glu Tyr Asp Val Leu Asp Lys Arg Arg
            405                 410                415

Gly Arg Asp Pro Glu Met Gly Gly Lys Pro Arg Arg Lys Asn Pro Gln
                420               425               430

Glu Gly Asn Glu Leu Gln Lys Asp Lys Met Ala Glu Ala Tyr Ser Glu
            435                 440               445

Ile Gly Met Lys Gly Glu Arg Arg Arg Gly Lys Gly His Asp Gly Gln
450                 455               460

Gly Leu Ser Thr Ala Thr Lys Asp Thr Tyr Asp Ala Leu His Met Gln
465                 470               475                 480

Ala Leu Pro Pro Arg
                485

<210> SEQ ID NO 15
<211> LENGTH: 726
<212> TYPE: DNA
<213> ORGANISM: Artificial Sequence
<220> FEATURE:
<223> OTHER INFORMATION: anti-CD19 scvf

<400> SEQUENCE: 15
gacatccaga tgacacagac tacatcctcc ctgtctgcct ctctgggaga cagagtcacc     60
atcagttgca gggcaagtca ggacattagt aaatatttaa attggtatca gcagaaacca    120
gatggaactg ttaaactcct gatctaccat acatcaagat tacactcagg agtcccatca    180
aggttcagtg gcagtgggtc tggaacagat tattctctca ccattagcaa cctggagcaa    240
gaagatattg ccacttactt tgccaacag ggtaatacgc ttccgtacac gttcggaggg     300
gggaccaagc tggagatcac aggtggcggt ggctcgggcg gtggtgggtc gggtggcggc    360
ggatctgagg tgaaactgca ggagtcagga cctggcctgg tggcgccctc acagagcctg    420
tccgtcacat gcactgtctc aggggtctca ttacccgact atggtgtaag ctggattcgc    480
cagcctccac gaaagggtct ggagtggctg ggagtaatat ggggtagtga aaccacatac    540
tataattcag ctctcaaatc cagactgacc atcatcaagg acaactccaa gagccaagtt    600
ttcttaaaaa tgaacagtct gcaaactgat gacacagcca tttactactg tgccaaacat    660
tattactacg gtggtagcta tgctatggac tactggggcc aaggaacctc agtcaccgtc    720
tcctca                                                               726

<210> SEQ ID NO 16
<211> LENGTH: 242
<212> TYPE: PRT
<213> ORGANISM: Artificial Sequence
<220> FEATURE:
<223> OTHER INFORMATION: anti-CD19 scvf

<400> SEQUENCE: 16

Asp Ile Gln Met Thr Gln Thr Thr Ser Ser Leu Ser Ala Ser Leu Gly
1               5                  10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
```

```
                    50                  55                  60
Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
   130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
   210                 215                 220

Gly Ser Tyr Ala Met Asp Tyr Trp Gly Gln Gly Thr Ser Val Thr Val
225                 230                 235                 240

Ser Ser
```

<210> SEQ ID NO 17
<211> LENGTH: 1485
<212> TYPE: DNA
<213> ORGANISM: Artificial Sequence
<220> FEATURE:
<223> OTHER INFORMATION: SP-CD19binder-CD8link-CD8tm-signaling LTG1494

<400> SEQUENCE: 17

```
atgctgctgc tggtgaccag cctgctgctg tgcgaactgc cgcatccggc gtttctgctg      60
attccggata ccgatattca gatgacccag accaccagca gcctgagcgc gagcctgggc     120
gatcgcgtga ccattagctg ccgcgcgagc caggatatta gcaaatatct gaactggtat     180
cagcagaaac cggatggcac cgtgaaactg ctgatttatc ataccagccg cctgcatagc     240
ggcgtgccga ccgctttagc ggcagcggc agcggcaccg attatagcct gaccattagc     300
aacctggaac aggaagatat tgcgacctat ttttgccagc agggcaacac cctgccgtat     360
acctttggcg gcggcaccaa actggaaatt accggcagca ccagcggcag cggcaaaccg     420
ggcagcggcg aaggcagcac caaaggcgaa gtgaaactgc aggaaagcgg cccgggcctg     480
gtggcgccga gccagagcct gagcgtgacc tgcaccgtga gcggcgtgag cctgccggat     540
tatggcgtga gctggattcg ccagccgccg cgcaaaggcc tggaatggct gggcgtgatt     600
tggggcagcg aaaccaccta ttataacagc gcgctgaaaa gccgcctgac cattattaaa     660
gataacagca aaagccaggt gtttctgaaa atgaacagcc tgcagaccga tgataccgcg     720
atttattatt gcgcgaaaca ttattattat ggcggcagct atgcgatgga ttattggggc     780
cagggcacca gcgtgaccgt gagcagcgcg gcggcgacca ccaccccggc gccgcgcccg     840
ccgaccccgg cgccgaccat tgcgagccag ccgctgagcc tgcgcccgga agcgtgccgc     900
ccggcggcgg gcggcgcggt gcatacccgc ggcctggatt ttgcgtgcga tatttatatt     960
```

-continued

```
tgggcgccgc tggcgggcac ctgcggcgtg ctgctgctga gcctggtgat tacccctgtat    1020 tgcaaacgcg ccgcaaaaa actgctgtat attttaaac agccgttat gcgcccggtg          1080 cagaccaccc aggaagaaga tggctgcagc tgccgctttc cggaagaaga agaaggcggc      1140
tgcgaactgc gcgtgaaatt tagccgcagc gcggatgcgc cggcgtatca gcagggccag      1200
aaccagctgt ataacgaact gaacctgggc cgccgcgaag aatatgatgt gctggataaa      1260
cgccgcggcc gcgatccgga aatgggcggc aaaccgcgcc gcaaaaaccc gcaggaaggc      1320
ctgtataacg aactgcagaa agataaaatg gcggaagcgt atagcgaaat ggcatgaaa       1380 ggcgaacgcc gccgcggcaa aggccatgat ggcctgtatc agggcctgag caccgcgacc      1440
aaagatacct atgatgcgct gcatatgcag gcgctgccgc cgcgc                      1485
```

<210> SEQ ID NO 18
<211> LENGTH: 491
<212> TYPE: PRT
<213> ORGANISM: Artificial Sequence
<220> FEATURE:
<223> OTHER INFORMATION: SP-CD19binder-CD8link-CD8tm-signaling LTG1494

<400> SEQUENCE: 18

```
Met Leu Leu Leu Val Thr Ser Leu Leu Leu Cys Glu Leu Pro His Pro
1               5                   10                  15

Ala Phe Leu Leu Ile Pro Asp Thr Asp Ile Gln Met Thr Gln Thr Thr
            20                  25                  30

Ser Ser Leu Ser Ala Ser Leu Gly Asp Arg Val Thr Ile Ser Cys Arg
        35                  40                  45

Ala Ser Gln Asp Ile Ser Lys Tyr Leu Asn Trp Tyr Gln Gln Lys Pro
    50                  55                  60

Asp Gly Thr Val Lys Leu Leu Ile Tyr His Thr Ser Arg Leu His Ser
65                  70                  75                  80

Gly Val Pro Ser Arg Phe Ser Gly Ser Gly Ser Gly Thr Asp Tyr Ser
                85                  90                  95

Leu Thr Ile Ser Asn Leu Glu Gln Glu Asp Ile Ala Thr Tyr Phe Cys
            100                 105                 110

Gln Gln Gly Asn Thr Leu Pro Tyr Thr Phe Gly Gly Gly Thr Lys Leu
        115                 120                 125

Glu Ile Thr Gly Ser Thr Ser Gly Ser Gly Lys Pro Gly Ser Gly Glu
    130                 135                 140

Gly Ser Thr Lys Gly Glu Val Lys Leu Gln Glu Ser Gly Pro Gly Leu
145                 150                 155                 160

Val Ala Pro Ser Gln Ser Leu Ser Val Thr Cys Thr Val Ser Gly Val
                165                 170                 175

Ser Leu Pro Asp Tyr Gly Val Ser Trp Ile Arg Gln Pro Pro Arg Lys
            180                 185                 190

Gly Leu Glu Trp Leu Gly Val Ile Trp Gly Ser Glu Thr Thr Tyr Tyr
        195                 200                 205

Asn Ser Ala Leu Lys Ser Arg Leu Thr Ile Ile Lys Asp Asn Ser Lys
    210                 215                 220

Ser Gln Val Phe Leu Lys Met Asn Ser Leu Gln Thr Asp Asp Thr Ala
225                 230                 235                 240

Ile Tyr Tyr Cys Ala Lys His Tyr Tyr Tyr Gly Gly Ser Tyr Ala Met
                245                 250                 255

Asp Tyr Trp Gly Gln Gly Thr Ser Val Thr Val Ser Ser Ala Ala Ala
            260                 265                 270
```

```
Thr Thr Thr Pro Ala Pro Arg Pro Pro Thr Pro Ala Pro Thr Ile Ala
            275                 280                 285

Ser Gln Pro Leu Ser Leu Arg Pro Glu Ala Cys Arg Pro Ala Ala Gly
        290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Ser Leu Val
                325                 330                 335

Ile Thr Leu Tyr Cys Lys Arg Gly Arg Lys Lys Leu Leu Tyr Ile Phe
                340                 345                 350

Lys Gln Pro Phe Met Arg Pro Val Gln Thr Thr Gln Glu Glu Asp Gly
                355                 360                 365

Cys Ser Cys Arg Phe Pro Glu Glu Glu Glu Gly Gly Cys Glu Leu Arg
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
                420                 425                 430

Arg Arg Lys Asn Pro Gln Glu Gly Asn Glu Leu Gln Lys Asp Lys Met
            435                 440                 445

Ala Glu Ala Tyr Ser Glu Ile Gly Met Lys Gly Glu Arg Arg Arg Gly
        450                 455                 460

Lys Gly His Asp Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 19
<211> LENGTH: 1470
<212> TYPE: DNA
<213> ORGANISM: Artificial Sequence
<220> FEATURE:
<223> OTHER INFORMATION: SP-CD19binder-CD8link-CD8tm-signals (LTI
      re-engineered) (CTG 1538)

<400> SEQUENCE: 19
atgctgctgc tggtgaccag cctgctgctg tgcgaactgc cgcatccggc gtttctgctg      60
attccggata ttcagatgac ccagaccacc agcagcctga gcgcgagcct gggcgatcgc     120
gtgaccatta gctgccgcgc gagccaggat attagcaaat atctgaactg gtatcagcag     180
aaaccggatg gcaccgtgaa actgctgatt tatcatacca gccgcctgca tagcggcgtg     240
ccgagccgct ttagcggcag cggcagcggc accgattata gcctgaccat tagcaacctg     300
gaacaggaag atattgcgac ctattttgc cagcagggca cacccctgcc gtataccttt     360
ggcggcggca ccaaactgga attaccggc ggcggcggca gcggcggcgg cggcagcggc     420
ggcggcggca gcgaagtgaa actgcaggaa agcggcccgg gcctggtggc gccgagccag     480
agcctgagcg tgacctgcac cgtgagcggc gtgagcctgc cggattatgg cgtgagctgg     540
attcgccagc cgccgcgcaa aggcctgaa tggctgggcg tgatttgggg cagcgaaacc     600
acctattata cagcgcgct gaaaagccgc ctgaccatta ttaaagataa cagcaaaagc     660
caggtgtttc tgaaaatgaa cagcctgcag accgatgata ccgcgattta ttattgcgcg     720
aaacattatt attatggcgg cagctatgcg atggattatt ggggccaggg caccagcgtg     780
```

-continued

```
accgtgagca gcgcggcggc gaccaccacc ccggcgccgc gcccgccgac cccggcgccg    840
accattgcga gccagccgct gagcctgcgc ccggaagcgt gccgcccggc ggcgggcggc    900
gcggtgcata cccgcggcct ggattttgcg tgcgatattt atatttgggc gccgctggcg    960
ggcacctgcg cgtgctgct gctgagcctg gtgattaccc tgtattgcaa acgcggccgc   1020
aaaaaactgc tgtatatttt taaacagccg tttatgcgcc cggtgcagac cacccaggaa   1080
gaagatggct gcagctgccg ctttccggaa gaagaagaag gcggctgcga actgcgcgtg   1140
aaatttagcc gcagcgcgga tgcgccggcg tatcagcagg gccagaacca gctgtataac   1200
gaactgaacc tgggccgccg cgaagaatat gatgtgctgg ataaacgccg cggccgcgat   1260
ccggaaatgg gcggcaaacc gcgccgcaaa aacccgcagg aaggcctgta taacgaactg   1320
cagaaagata aaatggcgga agcgtatagc gaaattggca tgaaaggcga acgccgccgc   1380
ggcaaaggcc atgatggcct gtatcagggc ctgagcaccg cgaccaaaga tacctatgat   1440
gcgctgcata tgcaggcgct gccgccgcgc                                   1470
```

<210> SEQ ID NO 20
<211> LENGTH: 486
<212> TYPE: PRT
<213> ORGANISM: Artificial Sequence
<220> FEATURE:
<223> OTHER INFORMATION: SP-CD19binder-CD8link-CD8tm-signals (LTI re-engineered) (LTG 1538)

<400> SEQUENCE: 20

```
Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240
```

```
Lys His Tyr Tyr Tyr Gly Gly Ser Tyr Ala Met Asp Tyr Trp Gly Gln
              245                 250                 255

Gly Thr Ser Val Thr Val Ser Ser Ala Ala Thr Thr Thr Pro Ala
            260             265             270

Pro Arg Pro Pro Thr Pro Ala Pro Thr Ile Ala Ser Gln Pro Leu Ser
            275             280             285

Leu Arg Pro Glu Ala Cys Arg Pro Ala Ala Gly Gly Ala Val His Thr
    290             295             300

Arg Gly Leu Asp Phe Ala Cys Asp Ile Tyr Ile Trp Ala Pro Leu Ala
305                 310             315                 320

Gly Thr Cys Gly Val Leu Leu Leu Ser Leu Val Ile Thr Leu Tyr Cys
                325             330             335

Lys Arg Gly Arg Lys Lys Leu Leu Tyr Ile Phe Lys Gln Pro Phe Met
                340             345             350

Arg Pro Val Gln Thr Thr Gln Glu Glu Asp Gly Cys Ser Cys Arg Phe
                355             360             365

Pro Glu Glu Glu Glu Gly Gly Cys Glu Leu Arg Val Lys Phe Ser Arg
    370             375             380

Ser Ala Asp Ala Pro Ala Tyr Gln Gln Gly Gln Asn Gln Leu Tyr Asn
385             390             395                 400

Glu Leu Asn Leu Gly Arg Arg Glu Glu Tyr Asp Val Leu Asp Lys Arg
                405             410             415

Arg Gly Arg Asp Pro Glu Met Gly Gly Lys Pro Arg Arg Lys Asn Pro
                420             425             430

Gln Glu Gly Asn Glu Leu Gln Lys Asp Lys Met Ala Glu Ala Tyr Ser
            435             440             445

Glu Ile Gly Met Lys Gly Glu Arg Arg Arg Gly Lys Gly His Asp Gly
        450             455             460

Gln Gly Leu Ser Thr Ala Thr Lys Asp Thr Tyr Asp Ala Leu His Met
465             470             475             480

Gln Ala Leu Pro Pro Arg
                485

<210> SEQ ID NO 21
<211> LENGTH: 4
<212> TYPE: PRT
<213> ORGANISM: Artificial Sequence
<220> FEATURE:
<223> OTHER INFORMATION: Synthetic peptide

<400> SEQUENCE: 21

Gly Phe Leu Gly
1
```